(12) United States Patent
Erle et al.

(10) Patent No.: US 12,150,461 B2
(45) Date of Patent: Nov. 26, 2024

(54) NICOTINAMIDE ADENINE DINUCLEOTIDE (NAD) COMPOSITIONS, METHODS OF MANUFACTURING THEREOF, AND METHODS OF USE THEREOF

(71) Applicant: Sovida Solutions Ltd., London (GB)

(72) Inventors: Hanns-Eberhard Erle, Bougy-Villars (CH); Johannes Holzmeister, Zürich (CH); Anne Abriat, Geneva (CH)

(73) Assignee: Sovida Solutions Ltd., London (GB)

( * ) Notice: Subject to any disclaimer, the term of this patent is extended or adjusted under 35 U.S.C. 154(b) by 0 days.

(21) Appl. No.: 18/289,200

(22) PCT Filed: Jan. 19, 2022

(86) PCT No.: PCT/IB2022/000021
§ 371 (c)(1),
(2) Date: Nov. 1, 2023

(87) PCT Pub. No.: WO2022/234336
PCT Pub. Date: Nov. 10, 2022

(65) Prior Publication Data
US 2024/0226007 A1    Jul. 11, 2024

Related U.S. Application Data

(60) Provisional application No. 63/183,714, filed on May 4, 2021.

(51) Int. Cl.
*A61P 17/00* (2006.01)
*A23J 3/16* (2006.01)
(Continued)

(52) U.S. Cl.
CPC . *A23J 3/20* (2013.01); *A23J 3/16* (2013.01); *A23J 3/18* (2013.01); *A23J 3/227* (2013.01);
(Continued)

(58) Field of Classification Search
None
See application file for complete search history.

(56) References Cited

U.S. PATENT DOCUMENTS 5,674,528 A   10/1997   Ogata et al.
5,688,526 A   11/1997   Okamoto et al.
(Continued)

FOREIGN PATENT DOCUMENTS

CN   110302091 A   * 10/2019   ............... A61K 8/64
EP   0615747 A1   9/1994
(Continued)

OTHER PUBLICATIONS

A. Wozniacka, P. Szajerski, J. Adamus, J. Gebicki, and A Sysa-Jedrzejowska. "In Search for New Antipsoriatic Agents: NAD+ Topical Composition." Skin Pharmacology and Physiology, vol. 20, 2007, pp. 37-42. (Year: 2007).*
(Continued)

*Primary Examiner* — Isaac Shomer
(74) *Attorney, Agent, or Firm* — Lowenstein Sandler LLP

(57) ABSTRACT

Disclosed herein are compositions that include nicotinamide adenine dinucleotide (NAD), precursors thereof, derivatives thereof, or mixtures thereof encapsulated in a liposome, wherein the compositions exhibit enhanced chemical, physical, and/or microbial storage stability at a variety of storage temperatures. In certain embodiments, the compositions are stable and have positive permeability and senescence results. Also disclosed herein are methods for preparing such compositions and methods of using such compositions.

5 Claims, 8 Drawing Sheets

(51) Int. Cl.
| | |
|---|---|
| A23J 3/18 | (2006.01) |
| A23J 3/20 | (2006.01) |
| A23J 3/22 | (2006.01) |
| A23J 3/26 | (2006.01) |
| A23L 5/10 | (2016.01) |
| A23L 5/46 | (2016.01) |
| A61K 9/127 | (2006.01) |
| A61K 31/7084 | (2006.01) |

(52) U.S. Cl.
CPC . *A23J 3/26* (2013.01); *A23L 5/10* (2016.08); *A23L 5/46* (2016.08); *A61K 9/1272* (2013.01); *A61K 31/7084* (2013.01); *A61P 17/00* (2018.01); *A23V 2002/00* (2013.01)

(56) References Cited

U.S. PATENT DOCUMENTS

| | | | |
|---|---|---|---|
| 2007/0231377 A1 | 10/2007 | Abou-Nemeh | |
| 2008/0233183 A1* | 9/2008 | McCook | A61K 47/34 424/94.1 |
| 2009/0246234 A1 | 10/2009 | Johnson | |
| 2012/0171280 A1 | 7/2012 | Zhang | |
| 2013/0202683 A1 | 8/2013 | McCook et al. | |
| 2014/0079761 A1* | 3/2014 | Perricone | A61K 9/0014 424/450 |
| 2014/0234428 A1* | 8/2014 | Barathur | A61K 47/14 514/249 |
| 2016/0120857 A1* | 5/2016 | Ghahary | A61K 31/198 514/567 |
| 2016/0168613 A1* | 6/2016 | Ayyub | C12N 11/04 435/177 |
| 2016/0184228 A1* | 6/2016 | Morrison | A61K 31/192 514/629 |
| 2016/0250241 A1* | 9/2016 | Deren-Lewis | A61P 17/00 514/43 |
| 2016/0271245 A1* | 9/2016 | Hearl | A61K 39/35 |
| 2016/0279161 A1 | 9/2016 | Wu et al. | |
| 2021/0213107 A1 | 7/2021 | Moser et al. | |
| 2021/0251917 A1* | 8/2021 | Sloat | A61K 31/352 |
| 2022/0354879 A1* | 11/2022 | Holzmeister | A61K 9/0019 |

FOREIGN PATENT DOCUMENTS

| | | |
|---|---|---|
| EP | 0687463 A1 | 12/1995 |
| EP | 0 722 734 A1 | 7/1996 |
| WO | 2014/059034 A2 | 4/2014 |
| WO | 2015070280 A1 | 5/2015 |
| WO | 2017/147058 A1 | 8/2017 |

OTHER PUBLICATIONS

Barbara Stussman, Ashley Williams, Joseph Snow, Angelique Gavin, Remle Scott, Avindra Nath, and Brian Walitt. "Characterization of Post-exertional Malaise in Patients With Myalgic Encephalomyelitis/Chronic Fatigue Syndrome." Frontiers in Neurology, vol. 11, Article 1025, Sep. 2020, pp. 1-17. (Year: 2020).*
Peter Belenky, Katrina L. Bogan and Charles Brenner. "NAD+ metabolism in health and disease." TRENDS in Biochemical Sciences, vol. 32, No. 1, 2006, pp. 13-19 followed by a two page update. (Year: 2006).*
Annie-Louise Robson et al. "Advantages and Limitations of Current Imaging Techniques for Characterizing Liposome Morphology." Frontiers in Pharmacology, vol. 9, Article 80, Feb. 2018, pp. 1-8. (Year: 2018).*
Balamurugan K and Chintamani P. "Lipid nano particulate drug delivery: An overview of the emerging trend." The Pharma Innovation Journal, vol. 7(7), 2018; pp. 779-789. (Year: 2018).*
J Mei, J Qian, X-c Zhang, J-b Fang, J-F Wu, and Y Jiang. English translation of CN 110302091 A. "Anti-skin Aging Composition Containing Nicotinamide Adenine Dinucleotide And Preparation Method And Application Thereof." Originally published in Chinese on Oct. 8, 2019, 18 printed pages. (Year: 2019).*
International Search Report of International Application No. PCT/IB2022/000021 mailed Aug. 5, 2022, 17 pgs.
Mendelsohn, et al., "Interacting NAD+ and Cell Senescene Pathways Complicate Antiaging Therapies", Rejuvenation Research, Jun. 1, 2019, pp. 261-266, vol. 22, No. 3.
Amjad et al., "Role of NAD+ in regulating cellular and metoabolic signaling pathways", Molecular Metabolism, Feb. 17, 2021, 17 pgs., vol. 19.
Csiszar et al., "Role of endothelial NAD+ deficiency in age-related vascular dysfunction", American Journal of Physiology Heart and Circulatory Physiology, Jun. 1, 2019, pp. H1253-H1266, vol. 316, No. 6.
Fang et al., "Nicotinamide mononucleotide ameliorates senescence in alveolar epithelial cells", MEDCOM, Feb. 7, 2021, pp. 279-287, vol. 2, No. 2.
Lenglah, Naruemon, "i Skin Permeation Study of Liposomes Containing Nicotinamide for Cosmeceutical Application A Thesis Submitted in Partial Fulfillment of the Requirements for the Degree of Master of Pharmacy in Pharmaceutical Sciences", Jan. 1, 2012.
Ho et al., "Faces of cellular senescence in skin aging", Mechanisms of Ageing and Development, Jun. 21, 2021, p. 13 pgs, vol. 198.
Han, et al., Research Communications in Molecular Pathology and Pharmacology, vol. 110, Nos. 1 & 2, pp. 107-116, 2001.
Giacomoni, P., "Sunscreens, suntan and anti-sun-burn preparations today", vol. 20, pp. 129-136, 2002.
Kapoor et al., "Stable Liposome in Cosmetic Platforms for Transdermal Folic Acid Delivery For Fortification and Treatment of Micronutrient Deficiencies", Scientific Reports, Oct. 31, 2018, 12 pages.
Humiston, John E. M.D., Pharmacy Compounding Committee Review: Nicotinamide Adenine Dinucleotide (NAD+1), Fagron North America: Nominator, 2017, 68 pages.
Gutekunst et al. "The Natural Way into the Skin, Encapsulation of Active Ingredients is an Increasingly Important Tool in Personal Care", 2019, 4 pages.
Lowry et al. "The Stability of Pyridine Nucleotides", The Journal of Biological Chemistry, vol. 236, No. 10, Oct. 1961, 4 pages.

* cited by examiner

*Figure 7.* Cell survival results in human aortic endothelial cells (HAECs) (A) Comparison among untreated cells and cells treated with different concentrations of LIPONAD. (B) Comparison between cells treated with NAD+ alone and LIPONAD.

FIG. 8

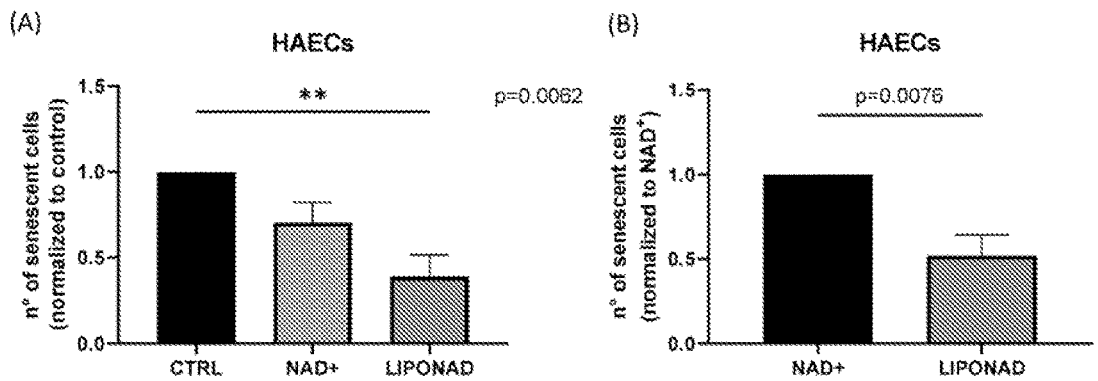

*Figure 8.* Cellular senescence results in human aortic endothelial cells (HAECs) (A) Comparison among untreated cells, cells treated with NAD+ and LIPONAD. (B) Comparison between cells treated with NAD+ alone and LIPONAD.

FIG. 9

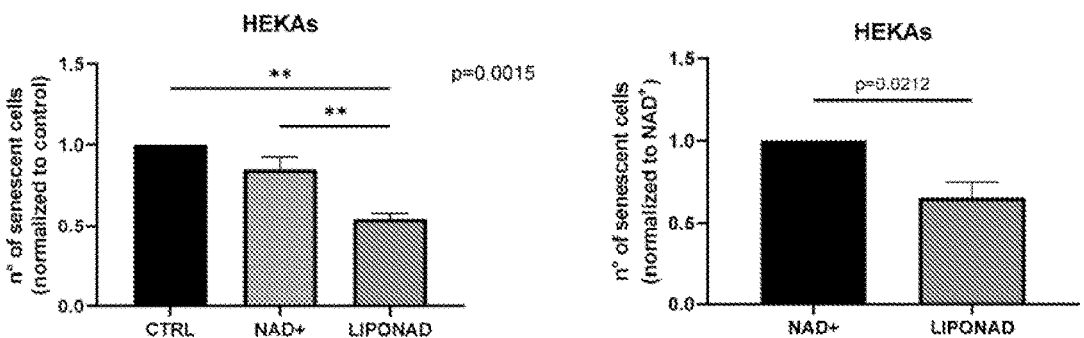

*Figure 9.* Cellular senescence results in human epidermal keratinocytes (HEKas) (A) Comparison among untreated cells, cells treated with NAD+ and LIPONAD. (B) Comparison between cells treated with NAD+ alone and LIPONAD.

NICOTINAMIDE ADENINE DINUCLEOTIDE (NAD) COMPOSITIONS, METHODS OF MANUFACTURING THEREOF, AND METHODS OF USE THEREOF

CROSS-REFERENCE TO RELATED APPLICATIONS

The present application is a national stage entry under 35 USC § 371 of International Application No. PCT/IB2022/000021 filed on Jan. 19, 2022, which claims priority to U.S. Provisional Patent Application No. 63/183,714 filed on May 4, 2021, the contents of which are incorporated herein by reference in their entirety.

FIELD OF THE DISCLOSURE

The present disclosure relates to compositions that include nicotinamide adenine dinucleotide, derivatives thereof, precursors thereof, or a combination thereof. In certain embodiments, the compositions are stable and have positive permeability and senescence results. The present disclosure also relates to methods of preparing such compositions, and to methods of using such compositions.

BACKGROUND OF THE DISCLOSURE

The oxidized form of extracellular β-nicotinamide adenine dinucleotide (NAD+) is a very important cofactor for many redox reactions in living cells and a substrate for numerous enzymes[1] ([1] Kim U H, Han M K, Park B H, Kim H R, An N H: Function of NAD glycohydrolase in ADP-ribose uptake from NAD by human erythrocytes. Biochim Biophys Acta 1993; 1178: 121-126; Lee H C, Aarhus R: ADP-ribosyl cyclase: an enzyme that catalyzes NAD+into a calciummobilizing metabolite. Cell Regul 1991; 2: 203-209; Travo P, Muller H, Shuber F: Calf spleen NAD glycohydrolase. Comparison of the catalytic properties of the membrane-bound and the hydrosoluble forms of the enzyme. Eur J. Biochem 1979; 96:141-149). As such, NAD+ may potentially have beneficial properties in mitigating various conditions.

Despite the above, the uses of NAD+, its precursors, and/or its derivatives is limited due to their limited stability. For instance, NAD+ is known to be relatively unstable[2] ([2] Ganti T, Fodor J: Studies on the kinetics of NAD-decomposition. Acta Physiol Acad Sci Hung 1965; 26: 199-205; Lawry O H, Passonneau J V, Rock M K: The stability of pyridine nucleotides. J Biol Chem 1961; 236: 2756-2759.). Various efforts have been undertaken in attempts to stabilize NAD+[3] ([3] A. Wozniacka, P. Szajerski, J. Adamus, J. Gebicki, A. Sysa-Jedrzejowska: In Search of New Antipsoriatic Agents: NAD$^+$ Topical Composition. Skin Pharmacol. Physiol. 2007:20:37-42.), however, long term stability outside refrigerated conditions remains a challenge.

Accordingly, it is an ongoing effort to identify a composition that includes NAD+, its precursors, and/or its derivatives and maintains long term storage stability (e.g., one or more of chemical, physical, and/or microbial stability) at a variety of storage conditions (e.g., a variety of temperatures).

SUMMARY OF THE DISCLOSURE

In certain embodiments, the present disclosure is directed to a composition that includes a liposome and an active agent encapsulated in the liposome, wherein the active agent includes nicotinamide adenine dinucleotide (NAD+), a precursor thereof, a derivative thereof, or a combination thereof.

In certain embodiments, the composition maintains more than about 90 wt %, more than about 92 wt %, more than about 94 wt %, more than about 96 wt %, more than about 98 wt %, more than about 99 wt %, or about 100 wt % of the NAD+, the precursor thereof, the derivative thereof, or the mixture thereof is maintained after storage at a temperature of about 2° C. to about 8° C., about 20° C. to about 30° C., or about 35° C. to about 45° C. for a duration of about 1 month, about 3 months, about 6 months, or about 12 months, as compared to the weight of the NAD+, the precursor thereof, the derivative thereof, or the mixture thereof in the composition before storage (t=0).

In certain embodiments, the active agent in the composition is selected from nicotinic acid (NA), nicotinamide (NAM), nicotinamide mononucleotide (NMN), nicotinamide riboside (NR), nicotinamide adenine dinucleotide plus hydrogen (NADH), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+), or a mixture thereof. In one embodiment, the active agent includes NAD+.

In certain embodiments, the liposome in the composition includes a vesicle forming lipid, which may be selected from phosphatidylcholine (PC), phosphatidylethanolamine (PE), phosphatidic acid (PA), phosphatidylinositol (PI), sphingomyelin (SM), polyvinylpyrrolidone, polyvinylmethylether, polymethyloxazoline, polyethyloxazoline, polyhydroxypropyloxazoline, polyhydroxypropylmethacry lamide, polymethacry lamide, polydimethylacry lamide, polyhydroxypropylmethacry late, polyhydroxyethylacrylate, hydroxymethylcellulose, hydroxyethylcellulose, polyethyleneglycol, polyaspartamide, lecithin, dipalmitoyl lecithin, distearoylphosphatidylcholine, or a mixture thereof. In one embodiment, the vesicle forming lipid includes lecithin.

In certain embodiments, the composition further includes one or more additional excipients.

In certain embodiments, the one or more additional excipients include a solvent, such as, without limitations, an alcohol, water, or a mixture thereof. In certain embodiments, the solvent includes an alcohol selected from ethanol, isopropanol, propylene glycol, glycerol, ethylene glycol, ethylene glycol monoethyl, monobutyl ether, propylene glycol monomethyl, propylene glycol monoethyl ether, propylene glycol monobutyl ether, diethylene glycol monomethyl, diethylene glycol monomethyl ether, diethylene glycol monoethyl ether, butylene glycol, pentylene glycol, sorbitol, or a mixture thereof. In one embodiment, the solvent includes water, glycerol, and pentylene glycol.

In certain embodiments, the one or more additional excipients includes a pH adjusting agent, which may be selected from sodium hydroxide, potassium hydroxide, calcium hydroxide, sodium citrate, sodium acetate, magnesium hydroxide, citric acid, hydrochloric acid, or a mixture thereof. In certain embodiments, the pH adjusting agent is present in the composition at an effective amount to adjust the pH of the composition to range from about 5 to about 9, from about 5.5 to about 8.5, or from about 6 to about 7.

In certain embodiments, the composition may include one or more additional excipients, such as, without limitations, carbohydrates, antioxidants, chelating agents, low-molecular weight proteins, high-molecular weight polymers, gel-forming agents, stabilizers, additives, wetting agents, emulsifying agents, surfactant and/or dispersing agents, alkalizing agents, coloring agents, synthetic dies, fillers, diluents, mineral oxides, preservatives, or a mixture thereof.

In certain embodiments, the composition is suitable for topical administration, oral administration, or parenteral administration.

In certain embodiments, the disclosure may be directed to a method for stabilizing an active agent that includes nicotinamide adenine dinucleotide (NAD+), a precursor thereof, a derivative thereof, or a combination thereof, by encapsulating the active agent in a liposome.

In certain embodiments, the disclosure may be directed to a method of preparing any of the compositions described herein. For example, the method may include forming a solution that includes an active agent, such as nicotinamide adenine dinucleotide (NAD+), a precursor thereof, a derivative thereof, or a combination thereof, and a solvent. In certain embodiments, the method may further include combining the active agent solution with a vesicle forming lipid. In certain embodiments, the method may further include combining the active agent solution and vesicle forming lipid with one or more additional excipients to form, e.g., an oral composition, a topical composition, or a parenteral composition.

In certain embodiments, the disclosure may be directed to a method of treating a condition by administering any of the compositions described herein to a subject in need thereof. In certain embodiments, the administration may be topical, oral, or parenteral.

In certain embodiments, the subject may be treated for one or more of loss of skin firmness, decrease of skin thickness, fine lines, wrinkles, loss of elasticity, sagging, dryness, age spots, diminished rate of turnover, abnormal desquamation, decrease of the density and disorganization of the extra-cellular matrix in the dermis and other histological changes, skin roughness, skin smoothness, brightness, radiance, UV damage, free radical damage, radiation damage, pollution damage, damage from environmental toxins or irritants or allergans, skin tone, weather-beaten appearance, yellowing, skin pores becoming less noticeable, hyperpigmentation, scars, skin surface irregularities, rosacea, exogenous eczema, acne, psoriasis, skin's regenerative and renewal process, redness, ichthyosis, lack of tactile smoothness, lack of visual smoothness, lack of softness, lack of luminosity, lack of radiance, skin texture, crow's feet, nasal fold, dyschromia, crepey skin texture, reduction in skin elasticity, and other damaging skin conditions.

In certain embodiments, the subject may be treated for one or more of fatigue (e.g., chronic fatigue syndrome), neurocognitive difficulties, sleep disturbance, postexertional malaise, headaches, muscle weakness, arthralgia, myalgias, allergy, swelling and tenderness of lymph nodes, depression, and other stress related conditions or conditions that could benefit from regulating cellular energy metabolism.

In certain embodiments, the compositions disclosed herein are utilized in methods of slowing skin aging.

In certain embodiments, the compositions disclosed herein are utilized in methods to improve the skin microcirculation.

In certain embodiments, the compositions disclosed herein are utilized in methods of decreasing skin tropism.

In certain embodiments, the compositions disclosed herein are utilized in methods of improving skin tone.

BRIEF DESCRIPTION OF THE DRAWINGS

The present disclosure is illustrated by way of example, and not by way of limitation, in the figures of the accompanying drawings, in which:

FIG. 8 is a graph representing the cellular senescence results in human aortic endothelial cells (HAECs).

FIG. 9 is a graph representing the cellular senescence results in human epidermal keratinocytes (HEKas).

DEFINITIONS

Figure 1:
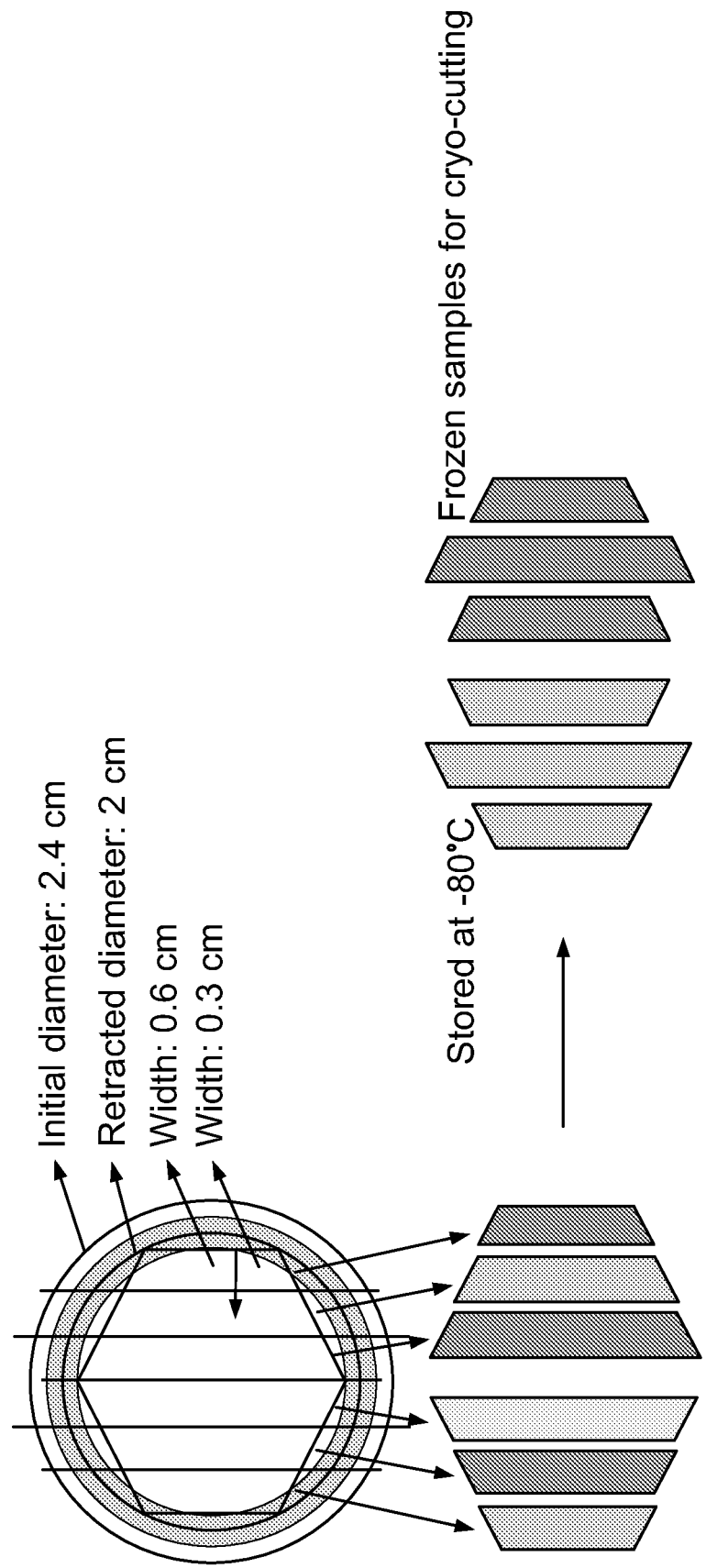
FIG. 1 illustrates how the explants of the permeability study were sectioned into six parts for analysis.

As used herein, the singular forms "a," "an," and "the" include plural references unless the context clearly indicates otherwise. Thus, for example, reference to "an active agent" includes a single active agent as well as a mixture of two or more different active agent, and reference to an "excipient" includes a single excipient as well as a mixture of two or more different excipients, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number±10%, such that "about 10" would include from 9 to 11.

As used herein, the terms "active agent," "active ingredient," and "active pharmaceutical ingredient" refer to any material that is intended to produce a therapeutic, prophylactic, or other intended effect, whether or not approved by a government agency for that purpose. These terms with respect to specific agents include all pharmaceutically active agents, all pharmaceutically acceptable salts thereof, complexes, stereoisomers, crystalline forms, co-crystals, ether, esters, hydrates, solvates, and mixtures thereof, where the form is pharmaceutically active.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

The term "patient" refers to a subject, an animal or a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are otherwise healthy.

"Pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

The term "condition" or "conditions" refers to those medical or cosmetic conditions that can be treated or prevented by administration to a subject of an effective amount of an active agent.

The terms "treatment of" and "treating" includes the lessening of the severity of or cessation of a condition or lessening the severity of or cessation of symptoms of a condition.

The terms "prevention of" and "preventing" includes the avoidance of the onset of a condition.

In certain embodiments, the terms "treatment" or "treating" with respect to a condition means administration with the intent to provide a pharmacodynamics effect, regardless of the outcome. In certain embodiments, "treatment" or "treating" means "having positive effect on a condition" and encompass reduction in the severity, amelioration, and/or alleviation of at least one symptom of a condition; a reduction, amelioration, and/or alleviation in the severity of the conditions; delay, prevention, or inhibition of the progression of the condition; or a perceived improvement or benefit as a result of the treatment. Treatment, as used herein, does not require total curing of the condition. In certain embodiments, a composition of the present disclosure may provide improvement to a patient's quality of life, or delay, prevent, inhibit the onset of one or more symptoms of a condition, or provide a perceived benefit. As used herein, these terms also encompass aesthetic improvements, e.g., to the skin, upon application of the disclosed active agents containing compositions.

The term "therapeutically effective amount" is intended to include an amount of an active agent, or an amount of the combination of active agents, e.g., to treat or prevent the condition, or to treat the symptoms of the condition, in a subject.

The term "effective amount" is intended to include an amount of a component, or an amount of a combination of component, to achieve a certain result or property, for instance, an effective amount of a pH adjusting agent to achieve a pH of 6.0 is intended to include an amount of one or more pH adjusting agents to arrive at a pH of 6.0.

The terms "application," "apply," and "applying" with respect to a disclosed topical composition, or method of using a disclosed topical composition, refer to any manner of administering a topical composition to the skin of a patient which, in medical or cosmetology practice, delivers the composition to the patient's skin surface. Smearing, rubbing, spreading, spraying a disclosed topical composition, with or without the aid of suitable devices, on a patient's skin are all included within the scope of the term "application," as used herein. The terms "topical" or "topically" with respect to administration or application of a disclosed formulation refer to epicutaneous administration or application, or administration onto skin.

As used herein, "oral delivery" or "oral administration" refers to a route of administration wherein the composition is taken through the mouth. Oral administration is a part of enteral administration, which also includes buccal (dissolved inside the cheek), sublabial (dissolved under the lip), and sublingual administration (dissolved under the tongue). In certain embodiments, oral administration includes a route of administration wherein the composition is ingested. In certain embodiments, oral administration includes a route of administration wherein the composition is inhaled.

As used herein, "parenteral administration" refers to a route of administration wherein the pharmaceutical dosage form is injected, e.g., to the muscle (intramuscular administration), to the vein (intravenous administration), under the skin (subcutaneous administration).

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The term "extended release" refers to an active agent that is released over a period of time, e.g., to provide a once daily or twice daily dosage form.

The term "immediate release" refers to a composition that allows the active agent to dissolve in the gastrointestinal tract, with no intention of delaying or prolonging the dissolution or absorption of the active agent. For instance, to the release of at least 85%, at least 90%, or at least 95% of an active agent in about 5 minutes, about 15 minutes, about 30 minutes, about 45 minutes or about 60 minutes, as measured by in-vitro dissolution in a USP Apparatus 1 (#40 mesh basket), in a USP Apparatus 2 (paddle), or in a USP Apparatus 3 (reciprocating cylinder) in aqueous media (pH 1-8) at room temperature.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

DETAILED DESCRIPTION

Composition

In certain embodiments, the instant disclosure is directed to stable compositions that include an active agent encapsulated in a liposome, wherein the active agent includes nicotinamide adenine dinucleotide (NAD+), a precursor thereof, a derivative thereof, or a combination thereof.

Nicotinamide adenine dinucleotide (NAD) includes two nucleotides joined through their phosphate groups. One nucleotide contains adenine nucleobase and the other nicotineamide. The oxidized form of NAD is abbreviated as NAD+ and the reduced form of NAD is abbreviated as NADH. The oxidized form of NAD is also sometimes referred to as "β-nicotinamide adenine dinucleotide" and as "free acid (NAD)."

NAD also has various precursors and derivatives, such as, without limitations, nicotinic acid (NA), nicotinamide (NAM), nicotinamide mononucleotide (NMN), nicotinamide riboside (NR), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+).

In certain embodiments, the active agent encapsulated in a liposome in any of the compositions described herein may be selected from nicotinic acid (NA), nicotinamide (NAM), nicotinamide mononucleotide (NMN), nicotinamide riboside (NR), nicotinamide adenine dinucleotide plus hydrogen (NADH), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+), or a mixture thereof. In one embodiment, the active agent encapsulated in a liposome in any of the compositions described herein may be NAD+.

In certain embodiments, the active agent (e.g., nicotinamide adenine dinucleotide (NAD+), a precursor thereof, a derivative thereof, or a combination thereof) in any of the compositions described herein may be present in an amount ranging from more than 0 wt % to about 20 wt %, from about 0.5 wt % to about 15 wt %, or from about 1 wt % to about 10 wt %, or any sub-range or single value therein, based on total weight of the composition. In certain embodiments, NAD+ may be present in the composition in an amount ranging from more than 0 wt % to about 20 wt %, from about 0.5 wt % to about 15 wt %, or from about 1 wt % to about 10 wt %, or any sub-range or single value therein, based on total weight of the composition. In certain embodiments, these concentrations refer to the amount of active agent in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the active agent may or may not fall within these ranges in various embodiments.

In certain embodiments, the active agent (e.g., nicotinamide adenine dinucleotide (NAD+), a precursor thereof, a derivative thereof, or a combination thereof) in any of the compositions described herein may be present in an amount ranging from any of more than (wt %, about 0.5 wt %, about 1 wt %, about 2 wt %, about 3 wt %, about 4 wt %, about 5 wt %, about 6 wt %, about 7 wt %, about 8 wt %, or about 9 wt % to any of about 10 wt %, about 11 wt %, about 12 wt %, about 13 wt %, about 14 wt %, about 15 wt %, about 16 wt %, about 17 wt %, about 18 wt %, about 19 wt %, or about 20 wt %, or any sub-range or single value therein, based on total weight of the composition. In certain embodiments, these concentrations refer to the amount of active agent in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the active agent may or may not fall within these ranges in various embodiments.

In certain embodiments, NAD+ may be present in any of the compositions described herein in an amount ranging from any of more than 0) wt %, about 0.5 wt %, about 1 wt %, about 2 wt %, about 3 wt %, about 4 wt %, about 5 wt %, about 6 wt %, about 7 wt %, about 8 wt %, or about 9) wt % to any of about 10 wt %, about 11 wt %, about 12 wt %, about 13 wt %, about 14 wt %, about 15 wt %, about 16 wt %, about 17 wt %, about 18 wt %, about 19 wt %, or about 20 wt %, or any sub-range or single value therein, based on total weight of the composition. In certain embodiments, these concentrations refer to the amount of NAD+ in a composition that includes (comprises, consists, or consists essentially of) the active agent, the liposome, and one or more additional excipients suitable forming a homogenous single phase liquid composition of the NAD+ encapsulated in the liposome. The instant disclosure also encompasses compositions that may include additional pharmaceutically acceptable excipients to form e.g., an oral composition, a topical composition, or a parenteral composition, and in such compositions, the concentrations of the NAD+ may or may not fall within these ranges in various embodiments.

Liposomes are formed when vesicle forming lipids (such as phospholipids and their derivatives) are dispersed in an aqueous solvent (such as water). Upon dispersion in aqueous solvent the vesicle forming lipids form closed vesicles called "liposomes", which are characterized by lipid bilayers encapsulating an aqueous core.

In certain embodiments, the liposome in any of the compositions described herein may include a vesicle forming lipid. In certain embodiments, the vesicle forming lipid may be selected from phosphatidylcholine (PC), phosphatidylethanolamine (PE), phosphatidic acid (PA), phosphatidylinositol (P1), sphingomyelin (SM), phosphatidylserine, phosphatidylglycerol, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide, lecithin, dipalmitoyl lecithin, distearoylphosphatidylcholine, or a mixture thereof. In one embodiment, the vesicle forming lipid includes lecithin.

In certain embodiments, the vesicle forming liquid in any of the compositions described herein may be present in an amount ranging from more than 0 wt % to about 20 wt %, from about 0.5 wt % to about 15 wt %, or from about 1 wt % to about 10 wt %, or any sub-range or single value therein, based on total weight of the composition. In certain embodiments, lecithin may be present in the composition in an amount ranging from more than 0 wt % to about 20 wt %, from about 0.5 wt % to about 15 wt %, or from about 1 wt % to about 10 wt %, or any sub-range or single value therein, based on total weight of the composition. In certain embodiments, these concentrations refer to the amount of vesicle forming agent in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the vesicle forming lipid may or may not fall within these ranges in various embodiments.

In certain embodiments, the vesicle forming lipid in any of the compositions described herein may be present in an amount ranging from any of more than 0 wt %, about 0.5 wt %, about 1 wt %, about 2 wt %, about 3 wt %, about 4 wt %, about 5 wt %, about 6 wt %, about 7 wt %, about 8 wt %, or about 9 wt % to any of about 10 wt %, about 11 wt %, about 12 wt %, about 13 wt %, about 14 wt %, about 15 wt %, about 16 wt %, about 17 wt %, about 18 wt %, about 19 wt %, or about 20 wt %, or any sub-range or single value therein, based on total weight of the composition. In certain embodiments, these concentrations refer to the amount of vesicle forming lipid in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the vesicle forming lipid may or may not fall within these ranges in various embodiments.

In certain embodiments, lecithin may be present in any of the compositions described herein in an amount ranging from any of more than 0 wt %, about 0.5 wt %, about 1 wt %, about 2 wt %, about 3 wt %, about 4 wt %, about 5 wt %, about 6 wt %, about 7 wt %, about 8 wt %, or about 9 wt % to any of about 10 wt %, about 11 wt %, about 12 wt %, about 13 wt %, about 14 wt %, about 15 wt %, about 16 wt %, about 17 wt %, about 18 wt %, about 19 wt %, or about 20 wt %, or any sub-range or single value therein, based on total weight of the composition. In certain embodiments, these concentrations refer to the amount of lecithin in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the lecithin may or may not fall within these ranges in various embodiments.

In certain embodiments the weight to weight ratio of the active agent to the vesicle forming lipid ranges from about 10:1 to about 1:10, about 8:1 to about 1:8, about 5:1 to about 1:5, about 3:1 to about 1:3, about 2:1 to about 1:2, about 1:1 to about 1:10, about 1:1 to about 1:8, about 1:1 to about 1:5, about 1:1 to about 1:3, or about 1:1 to about 1:2, or any sub-range or single value therein. In certain embodiments, the minimum amount of the active agent in the composition is a therapeutically effective amount. In certain embodiments, the maximum amount of the active agent in the composition is an effective amount to maintain a homogenous single liquid phase. In certain embodiments, the active agent is not added into the composition at an amount that would create a phase separation.

In certain embodiments, the composition further includes one or more additional excipients.

In certain embodiments, the one or more additional excipients include a solvent, such as, without limitations, an alcohol, water, or a mixture thereof. In certain embodiments, the solvent includes an alcohol selected from ethanol, isopropanol, propylene glycol, glycerol, ethylene glycol, ethylene glycol monoethyl, monobutyl ether, propylene glycol monomethyl, propylene glycol monoethyl ether, propylene glycol monobutyl ether, diethylene glycol monomethyl, diethylene glycol monomethyl ether, diethylene glycol monoethyl ether, butylene glycol, pentylene glycol, sorbitol, or a mixture thereof.

In certain embodiments, the solvent in any of the compositions described herein may be present in an amount ranging from about 70 wt % to about 98 wt %, from about 80 wt % to about 95 wt %, or from about 85 wt % to about 92 wt %, or any sub-range or single value therein, based on total weight of the composition. In certain embodiments, the solvent in any of the compositions described herein may be present in an amount ranging from any of about 70 wt %, about 72 wt %, about 74 wt %, about 76 wt %, about 78 wt %, about 80 wt %, about 82 wt %, about 84 wt %, about 85 wt %, or about 86 wt % to any of about 88 wt %, about 90 wt %, about 92 wt %, about 94 wt %, about 95 wt %, about 96 wt %, or about 98 wt %, or any sub-range or single value therein, based on total weight of the composition. In certain embodiments, these concentrations refer to the amount of solvent in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the solvent may or may not fall within these ranges in various embodiments.

In one embodiment, the solvent includes water, glycerol, and pentylene glycol.

In certain embodiments, the water in any of the compositions described herein may be present in an amount ranging from more than 0 wt % to about 50 wt %, from about 5 wt % to about 40 wt %, or from about 10 wt % to about 30 wt %, or any sub-range or single value therein, based on total weight of the composition. In certain embodiments, the water in any of the compositions described herein may be present in an amount ranging from any of more than 0 wt %, about 5 wt %, about 10 wt %, about 15 wt %, about 20 wt %, or about 25 wt % to any of about 30 wt %, about 35 wt %, about 40 wt %, about 45 wt %, or about 50 wt %, or any sub-range or single value therein, based on total weight of the composition. In certain embodiments, these concentrations refer to the amount of water in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the water may or may not fall within these ranges in various embodiments.

In certain embodiments, the glycerol in any of the compositions described herein may be present in an amount ranging from more than 0 wt % to about 90 wt %, from about 30 wt % to about 80 wt %, or from about 50 wt % to about 70 wt %, or any sub-range or single value therein, based on total weight of the composition. In certain embodiments, the glycerol in any of the compositions described herein may be present in an amount ranging from any of more than 0) wt %, about 5 wt %, about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, or about 90 wt %, or any sub-range or single value therein, based on total weight of the composition. In certain embodiments, these concentrations refer to the amount of glycerol in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the glycerol may or may not fall within these ranges in various embodiments.

In certain embodiments, the pentylene glycol in any of the compositions described herein may be present in an amount ranging from more than 0 wt % to about 20 wt %, from about 0.5 wt % to about 15 wt %, or from about 1 wt % to about 10 wt %, or any sub-range or single value therein, based on total weight of the composition. In certain embodiments, the pentylene glycol in any of the compositions described herein may be present in an amount ranging from any of more than (wt %, about 0.5 wt %, about 1 wt %, about 2 wt %, about 3 wt %, about 4 wt %, about 5 wt %, about 6 wt %, about 7 wt %, about 8 wt %, or about 9 wt % to any of about 10 wt %, about 11 wt %, about 12 wt %, about 13 wt %, about 14 wt %, about 15 wt %, about 16 wt %, about 17 wt %, about 18 wt %, about 19 wt %, or about 20 wt %, or any sub-range or single value therein, based on total weight of the composition. In certain embodiments, these concentrations refer to the amount of pentylene glycol in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the pentylene glycol may or may not fall within these ranges in various embodiments.

In certain embodiments, other inorganic solvents may be suitably used instead or in addition to pentylene glycol. Exemplary suitable solvents include, without limitations alcohols selected from ethanol, isopropanol, propylene glycol, glycerol, ethylene glycol, ethylene glycol monoethyl, monobutyl ether, propylene glycol monomethyl, propylene glycol monoethyl ether, propylene glycol monobutyl ether, diethylene glycol monomethyl, diethylene glycol monomethyl ether, diethylene glycol monoethyl ether, butylene glycol, pentylene glycol, sorbitol, or a mixture thereof. Any of these or other suitable solvents may be included at similar concentrations as described hereinabove for pentylene glycol.

In certain embodiments, the aqueous solvent that is utilized along with the vesicle forming lipids to form the liposomes is predominantly glycerol. Glycerol is self-conserving an exhibits microbial stability without necessarily including a preservative or a conservative. In certain embodiments, the compositions has less than about 20 wt %, less than about 15 wt %, less than about 10 wt %, less than about 8 wt %, less than about 5 wt %, less than about 3 wt %, less than about 1 wt %, less than about 0.5 wt %, less than about 0.1 wt %, or free (e.g., 0 wt %) of preservatives and/or conservatives.

In certain embodiments, the weight to weight ratio glycerol to other solvents in the compositions (such as water and/or pentylene glycol, individually or cumulatively together) ranges from about 15:1 to about 1:5, from about 10:1 to about 1:5, from about 8:1 to about 1:3, from about 5:1 to about 1:1, or from about 3:1 to about 1:5:1, or any sub-range or single value therein.

In certain embodiments, the one or more additional excipients includes a pH adjusting agent, which may be selected from sodium hydroxide, potassium hydroxide, calcium hydroxide, ammonium hydroxide, sulfuric acid, phosphoric acid, nitric acid, sodium citrate, sodium acetate, magnesium hydroxide, citric acid, hydrochloric acid, or a mixture thereof. In one embodiment, the pH adjusting agent is sodium hydroxide. In certain embodiments, the pH adjusting agent is present in the composition at an effective amount to adjust the pH of the composition to range from about 4 to about 9, from about 5.5 to about 8.5, or from about 6 to about 7.

In certain embodiments, the pH adjusting agent (e.g., sodium hydroxide) in any of the compositions described herein may be present in an amount of up to 5 wt %, up to about 4 wt %, up to about 3 wt %, up to about 2 wt %, or up to about 1 wt %, or any sub-range or single value therein, based on total weight of the composition. In certain embodiments, these concentrations refer to the amount of pH adjusting agent in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of the pH adjusting agent and/or the final pH of the composition may or may not fall within these ranges in various embodiments.

In certain embodiments, the compositions described herein have a pH ranging from any of about 4, about 4.3, about 4.5, about 4.7, about 5, about 5.3, about 5.5, about 5.8, about 6.0, about 6.2, about 6.5, about 6.8, or about 7 to any of about 7.3, about 7.5, about 7.7, about 8.0, about 8.3, about 8.5, about 8.7, or about 9.0, or any sub-range or single value therein.

In certain embodiments, the composition may include one or more additional excipients, such as, without limitations, carbohydrates, antioxidants, chelating agents, low-molecular weight proteins, high-molecular weight polymers, gel-forming agents, stabilizers, additives, wetting agents, emulsifying agents, surfactant and/or dispersing agents, alkalizing agents, coloring agents, synthetic dies, fillers, diluents, mineral oxides, preservatives, or a mixture thereof.

In certain embodiment, the composition further includes an antioxidant. In certain embodiments, the antioxidant may include trivalent phosphorous like e.g. phosphite, phenolic antioxidants, hydroxylamines, lactones such as substituted benzofuranones. Hindered phenols, thiosynergists and/or hindered amines are useful for the long-term stability for polymers, whereas the following antioxidants are suitable for use also in situation where the active substance is subject to oxidation: acids (ascorbic acid, erythorbic acid, etidronic acid, gallic acid, hypophosphorous acid, nordihydroguairetic acid, propionic acid etc.), phenols (e.g. BHA, BHT, t-butyl hydroquinone, dodecyl gallate, octyl gallate, 1,3,5-trihydroxybenzene), organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol. D-α-tocopherol. DL-α-tocopherol, tocopherol acetate, d-α-tocopheryl acetate, dl-α-tocopheryl acetate. However, other anti-oxidative agents known in the art may be used according to the present invention.

In certain embodiments, suitable antioxidants may include, without limitations, sterically hindered phenols, aryl amines, thioureas, thiocarbamates, phosphites, thioether esters, and combinations of the foregoing. Other suitable examples of antioxidants include, but are not limited to, alkylated monophenols, including but not limited to, 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol. 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1-yl)phenol and mixtures thereof, alkylthiomethylphenols, including but not limited to, 2,4-dioctylthiornethyl-6-tert-hutylphenol, 2,4-dioctylthiomethyl-6-methylphenol, 2,4-dioetylthiomethyl-6-ethylphenol. 2,6-di-dodecylthiornethyl-4-nonylphenol, hydroquinones and alkylated hydroquinones, including but not limited to, 2,6-di-tert-hutyl-4-methoxyphenol, 2,5-di-tert-butylhydroquinone, 2,5-di-tort-amylhydroquinone. 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate, tocopherols, including but not limited to, α-tocopherol, β-tocopherol, γ-tocopherol, 8-tocopherol and mixtures thereof (vitamin E), hydroxylated thiodiphenyl ethers, including but not limited to, 2,2'-thiobis(6-tort-butyl-4-methylphenol), 2,2'-thiobis(4-oetylphenol), 4,4'-thiobis(6-tert-butyl-3-methylphenol), 4,4'-thiobis(6-tert-butyl-2-methylphenol), 4,4'-thiobis(3,6-di-see-amylphenol), 4,4'-bis(2,6-dimethyl-4-hydroxyphenyl)-disulfide, alkylidenebisphenols, including but not limited to, 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol). 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-test-butyl-5-methyl-2-hydroxybenzyl)-4-methylphenol, 1.1.3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl] terephthalate, 1,1-bis-(3,5-dimethyl-2-hydroxyphenyl) butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,5,5-tetra-(5-tert-butyl-4-hydroxy-2-methylphenyl)pentane, O-, N- and S-benzyl compounds, including but not limited to, 3,5,3',5'-tetra-tert-butyl.-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxy benzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxy benzylmercaptoacetate, hydroxy benzylated malonates, including but not limited to, dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxy benzyl) malonate, bis[4-(1,1,3,3-tetramethylbutyl)phenyl]-2,2-bis (3,5-di-tert-butyl-4-hydroxy benzyl)malonate, aromatic hydroxybenzyl compounds, including but not limited to, 1,3,5-tris(3,5-di-tert-butyl-4-hydroxybenzyl)-2,4,6-trimethylbenzene, 1,4-bis(3,5-di-tert-butyl-4-hydroxy benzyl)-2,3,5,6-tetramethylbenzene, 2,4,6-tris(3,5-di-tert-butyl-4-hydroxy benzyl)phenol, triazine compounds, including but not limited to, 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxy benzyl) isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine. 1,3,5-tris(3,5-di-tert-butyl-4-hydroxy-phenylpropionyl)-hexahydro-1,3,5-triazine, 1,3,5-tris(3,5-dicyclohexyl-4-hydroxy benzyl)isocyanurate, benzylphosphonates, including but not limited to, dimethyl-2,5-di-tert-butyl-4-hydroxy benzylphosphonate, diethyl-3,5-di-tert-butyl-4-hydroxybenzylphosphonate, dioctadecyl3,5-di-tent-butyl-4-hydroxy benzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid, acylaminophenols, including but not limited to, 4-hydroxylauranilide, 4-hydroxystearanilide, octyl N-(3,5-di-tert-butyl-4-hydroxyphenyl)carbamate, esters of β-(3,5-di-tert-butyl-4-hydroxyphenyl)propionic acid with mono- or polyhydric alcohols. e.g. with methanol, ethanol n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaery thritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaery thritol, tris(hydroxyethyl)isocyanurate, N, N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane, esters of 6-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycal, thiodiethyl.ene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, amides of 6-(3,5-di-tert-butyl-4-hydroxyphenyl)propionic acid e.g. N,N'-bis(3,5-di-tert-butylA-N,N'-bis(3,5-di-tert-butyl-4-hydroxyphenylpropionyl)hexamethylenediamide, hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (Naugard RXL-1, supplied by Uniroyal), ascorbic acid (vitamin C), aminic antioxidants, including but not limited to, N,N'-di-isopropyl-p-phenylenediamine, N,N'-di-see-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine. N-(1,3-dimethylbutyl)-N'-phenyl-p-phenylenediamine, N-(1-methylheptyI)—N'-phenyl-p-phenylenediamine, N-cyclohexyl-N'-phenyl-p-phenvienediamine, 4-(p-toluenesulfamoyl)diphenylamine, N,N'-dimethyl-N,N'-di-see-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine. N-phenyl-2-naphthylamine, octylated diphenylamine, including but not limited to, p,p'-di-tert-octyldiphenylamine, 4-n-butylaminophenol, 4-butyrylaminophenol, 4-nonanoy-laminophenol, 4-dodecanoy laminophenol, 4-octadecanoy-laminophenol, bis(4-methoxyphenyl)amine 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane. 1,2-bis(phenylamino)propane, (o-tolyl)biguanide, bis[4-(1',3'-dimethylbutyl)phenyl] amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated teak-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N, N,N',N'-tetraphenyl-1,4-diaminobut-2-ene, and combinations of the foregoing.

In one embodiment, the antioxidant includes tocopherol. In certain embodiments, the antioxidant (e.g., tocopherol) in any of the compositions described herein may be present in an amount of up to about 0.5 wt %, up to about 0.4 wt %, up to about 0.3 wt %, up to about 0.2 wt %, or up to about 0.1 wt %, or any sub-range or single value therein, based on total weight of the composition. In certain embodiments, these concentrations refer to the amount of antioxidant in a composition that includes (comprises, consists, or consists essentially of) the active agent, the liposome, and one or more additional excipients suitable forming a homogenous single phase liquid composition of the active agent encapsulated in the liposome. The instant disclosure also encompasses compositions that may include additional pharmaceutically acceptable excipients to form e.g., an oral composition, a topical composition, or a parenteral composition, and in such compositions, the concentrations of antioxidant in the composition may or may not fall within these ranges in various embodiments.

In certain embodiments, the instant disclosure is directed to a composition that includes NAD+ encapsulated in a liposome. In one embodiment, the liposome includes a vesicle forming lipid that is lecithin. In one embodiment, the composition includes water and inorganic alcohols, such as, one or more of glycerol and/or pentylene glycol. In one embodiment, the composition includes pH adjusting agent, such as sodium hydroxide. In one embodiment, the composition includes an antioxidant, such as tocopherol.

In certain embodiments, the instant disclosure is directed to a liposomal composition of NAD+ including one or more of the following: a) more than 0 wt % to about 20 wt %, from about 0.5 wt % to about 15 wt %, or from about 1 wt % to about 10 wt % NAD+; b) more than 0 wt % to about 20 wt %, from about 0.5 wt % to about 15 wt %, or from about 1 wt % to about 10 wt % vesicle forming lipid (e.g., lecithin); c) more than 0 wt % to about 90 wt %, from about 30 wt % to about 80 wt %, from about 50 wt % to about 70 wt %, or from about 55 wt % to about 65 wt % glycerol; d) above 0 wt % to about 50 wt %, from about 5 wt % to about 40 wt %, or from about 10 wt % to about 30 wt % water; e) above 0 wt % to about 20 wt %, from about 0.5 wt % to about 15 wt %, or from about 1 wt % to about 10 wt % pentylene glycol; f) up to about 5 wt %, up to about 4 wt %, up to about 3 wt %, up to about 2 wt %, or up to about 1 wt % of a pH adjusting agent (e.g., sodium hydroxide); and/or g) up to about 0.5 wt %, up to about 0.4 wt %, up to about 0.3 wt %, up to about 0.2 wt %, or up to about 0.1 wt % of an antioxidant (e.g., tocopherol), wherein all wt % are based on the total weight of a) through g).

In certain embodiments, the instant disclosure may be further directed to a pharmaceutical composition, a cosmetic composition, a cosmeceutical composition, a nutraceutical composition, or a nutritional composition. The term "pharmaceutical composition" refers to a composition manufactured for use for medicinal purposes. The term "cosmeceutical composition" refers to a cosmetic composition scientifically proven to have medicinal properties. The term "cosmetic composition" refers to a composition refers to a composition that can maintain, protect, clean, add fragrance, change appearance, and the like without penetrating the skin or changing the functioning of the skin. The term "nutraceutical composition" refers to a composition which other than nutrition may also be used for medicinal purposes. The term "nutritional composition" refers to a supplement intended to supplement a subject's diet by providing additional nutrients.

In certain embodiments, the instant disclosure may be directed to an oral composition suitable for oral administration. In certain embodiments, the instant disclosure may be directed to a topical composition suitable for topical administration. In certain embodiments, the instant disclosure may be directed to an injectable composition suitable for parenteral administration.

Any of the pharmaceutical compositions, cosmetic compositions, cosmeceutical compositions, nutraceutical compositions, nutritional compositions, and the like (whether suitable for oral, topical, or parenteral administration) may include an active agent encapsulated in a liposome and a pharmaceutically acceptable excipient, wherein the active agent is selected from nicotinic acid (NA), nicotinamide (NAM), nicotinamide mononucleotide (NMN), nicotinamide riboside (NR), nicotinamide adenine dinucleotide plus hydrogen (NADH), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+), or a mixture thereof, preferably wherein the active agent includes NAD+.

In certain embodiments, suitable pharmaceutically acceptable excipients may include acrylics, cellulose derivatives, polysaccharides, monosaccharides, gums, natural or synthetic polymers (e.g., polyalkylene oxides (e.g., polymethylene oxides, polyethylene oxides, polypropylene oxides) polyethylenes, polypropylenes, polyvinyl chlorides, polycarbonates, polystyrenes, polyacrylates, polycaprolactone, polymethacrylates copolymers thereof, and mixtures thereof), liposomes, disintegrants (e.g., polyvinylpyrrolidone, sodium starch glycolate, crosscarmellose sodium, or a mixture thereof), glidants, lubricants, absorption enhancers, surfactants, binders, softeners, plasticizers (e.g., lecithin, hydrogenated vegetable oils, glycerol ester, lanolin, methyl ester, pentaerythritol ester, rice bran wax, stearic acid, sodium potassium stearates, and the like), waxes, fats, emulsifiers, fillers, antioxidants, flavors, colorants, diluents, processing aids (e.g., granulating aids), sweeteners such as those described above with respect to the chewable composition, fixing agents (e.g., polyols such as, without limitations, sorbitol, maltitol/isomalt, mannitol, starch, and the like). pH-adjusting agents, viscosity adjusting agents, solubility increasing or descreasing agents, osmotic agents, solvents, or a combination thereof.

In certain embodiments, suitable pharmaceutically acceptable excipients may include polyvinylpyrrolidone, natural and synthetic gums, polyvinyl alcohol, corn starch, hydrophilic and hydrophobic materials such as sustained release polymers, acrylic resins, protein-derived materials, waxes, shellacs, and solid or semi-solid oils such as hydrogenated castor oil and hydrogenated vegetable oil. More specifically, the controlled release materials can be, e.g., alkylcelluloses such as ethylcellulose, acrylic and methacrylic acid polymers and copolymers (e.g., acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, poly (methyl methacrylate), poly(methyl methacrylate) copolymer, polyacrylamide, aminoalkyl methacrylate copolymer, poly(methacrylic acid anhydride), glycidyl methacrylate copolymers, and mixtures of any of the foregoing), and cellulose ethers, such as hydroxyalkylcelluloses (e.g., hydroxypropylmethylcellulose) and carboxyalkylcelluloses. Waxes include, e.g., natural and synthetic waxes, fatty acids, fatty alcohols, and mixtures of the same (e.g., beeswax, carnauba wax, stearic acid and stearyl alcohol).

In certain embodiments, suitable pharmaceutically acceptable excipients may include gelling agents, such as and without limitation, sugars or sugar derived alcohols, such as mannitol, sorbitol, and the like, starch and starch derivatives, cellulose derivatives (such as microcrystalline cellulose, sodium caboxymethyl cellulose, methylcellulose, ethyl cellulose, hydroxyethyl cellulose, hydroxypropyl cellulose, hydroxypropyl methylcellulose, cellulose esters, cellulose diesters, cellulose triesters, cellulose ethers, cellulose ester-ethers, cellulose acylates, cellulose diacylates, cellulose triacylates, cellulose acetates, cellulose diacetates, cellulose triacetates, cellulose acetate propionates, cellulose acetate butyrates, cellulose acetate succinate, cellulose acetate phthalate, hydroxypropyl methyl cellulose phthalate, hydroxy propyl methyl cellulose acetate succinate (hypermellose acetate succinate), and mixtures thereof), attapulgites, bentonites, dextrins, alginates, algenic acid salts such as sodium alginate and potassium alginate, casein, stearic acid, shellac, carrageenan, gum tragacanth, gum acacia, gum arabic, pullulan gum, dextrin, gellan gum, agar gum, tara gum, karaya, guar gum, welan gum, rhamsan gum, locust bean gum, xanthan gum, pectin, gelatin, kaolin, lecithin, magnesium aluminum silicate, the carbomers and carbopols, polyvinylpyrrolidone, polyethylene glycol, polyethylene oxide, polyvinyl alcohol, silicon dioxide, surfactants, mixed surfactant/wetting agent systems, emulsifiers, other polymeric materials, and mixtures thereof.

In certain embodiments, suitable pharmaceutically acceptable excipients may include hydrophilic excipients, such as without limitations, water, low molecular weight polyols, such as, polyethylene glycol, polypropylene glycol, or a combination thereof. Examples of other suitable hydrophilic carriers include, without limitations, polyoxyethylene derivatives of a sorbitan ester, such as sorbitan monolaurate (Polysorbate 20), Polysorbate 80, Polysorbate 60, polyoxyethylene 20 sorbitan trioleate (Polysorbate 85), acetic acid, formic acid, other hydrophilic surfactants and mixtures thereof. Exemplary low molecular weight polyols include, without limitations, those having a number average molecular weight of from any of about 200 Dalton, about 400 Dalton, about 600 Dalton, about 800 Dalton, or about 1000 Dalton to any of about 2000 Dalton, about 3000 Dalton, about 4000 Dalton, about 5000 Dalton, about 6000 Da, or about 7000 Da, or any sub-range or single value therein (for instance, polyethylene glycol 400, polyethylene glycol 600, or the like).

In certain embodiments, suitable pharmaceutically acceptable excipients may include plasticizers, such as, but not be limited to, sugar alcohol plasticizer such as triacetin, isomalt, maltitol, xylitol, erythritol, adonitol, dulcitol, pentaerythritol, or mannitol; or polyol plasticizer such as diglycerin, ethylene glycol, diethylene glycol, triethyleneglycol, tetraethylene glycol, dipropylene glycol, a polyethylene glycol up to 10.000 MW, neopentyl glycol, propylene glycol. 1,3-propanediol, 2-methyl-1,3-propanediol, trimethylolpropane, a polyether polyol, ethanol amines; and mixtures thereof. Other exemplary plasticizers may also include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In certain embodiments, suitable pharmaceutically acceptable excipients may include plasticizer such as, without limitations, phosphate esters; phthalate esters; amides; mineral oils; fatty acids and esters; fatty alcohols, vegetable oils and hydrogenated vegetable oils including acetylated hydrogenated cottonseed glyceride and acetylated hydrogenated soy bean oil glycerides; acetyl tributyl citrate, acetyl triethyl citrate. Castor oil, diacetylated monoglycerides, dipropylene glycol salicylate glycerin, glyceryl cocoate, mono- and di-acetylated monoglycerides, nitrobenzene, carbon disulfide, fl-naphtyl salicylate, phthalyl glycolate, diocyl phthalate; sorbitol, sorbitol glyceryl tricitrate; sucrose octaacetate; a-tocopheryl polyethylene glycol succinate, phosphate esters; phthalate esters; amides; mineral oils; fatty acids and esters; fatty alcohols; and vegetable oils, fatty alcohols including cetostearyl alcohol, cetyl alcohol, stearyl alcohol, oleyl alcohol and myristyl alcohol; methyl abietate, acetyl tributyl citrate, acetyl triethyl citrate, diisooctyl adipate, amyl oleate, butyl ricinoleate, benzyl benzoate, butyl and glycol esters of fatty acids, butyl diglycol carbonate, butyl oleate, butyl stearate, di(beta-methoxyethyl) adipate, dibutyl sebacate, dibutyl tartrate, diisobutyl adipate, dihexyl adipate, triethylene glycol di(beta-ethyl butyrate), polyethylene glycol di(2-ethyl hexoate), diethylene glycol monolaurate, monomeric polyethylene ester, hydrogenated methyl ester of rosin, methoxyethyl oleate, butoxyethyl stearate, butyl phthalyl butyl glycolate, glycerol tributyrate, triethylene glycol dipelargonate, beta-(p-tert-amyl phenoxy) ethanol, beta-(p-tert-butytphenoxy)ethanol, beta-(p-tert-butytphenoxyethyl)acetate, bis(beta-p-tert-buthylphenoxydiethyl)ether, camphor, Cumar W-1, Cumar MH-1, Cumar V-1, diamyl phthalate, (diamylphenoxy) ethanol, diphenyl oxide, technical hydroabietyl alcohol, beckolin, benzene hexahydrochlonde, Clorafin 40, Piccolastic A-5, Piccalastic A-25, Flexol B-400, Glycerol alfa-methyl alfa-phenyl ether, chlorinated naphthalene, HB-40, monoamylphthalate, Nevillac 10 o-nitrodiphenyl and Paracril 26.

In certain embodiments, suitable pharmaceutically acceptable excipients may include plasticizer such as, without limitations, sugar alcohol plasticizer such as isomalt, maltitol, sorbitol, xylitol, erythritol, adonitol, dulcitol, pentaerythritol, or mannitol; or polyol plasticizer such as glycerin, diglycerin, ethylene glycol, diethylene glycol, triethyleneglycol, tetraethylene glycol, dipropylene glycol, a polyethylene glycol up to 10.000 MW, neopentyl glycol, propylene glycol. 1,3-propanediol, 2-methyl-1,3-propanediol, trimethylolpropane, a polyether polyol, ethanol amines; and mixtures thereof. Other exemplary plasticizers may include, without limitations, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, citrate ester-type plasticizers, and triacetin. Such plasticizers may include 1,2-butylene glycol, 2,3-butylene glycol, styrene glycol, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, glyceryl monostearate, polysorbate 80, acetyl triethyl citrate, tributyl citrate and allyl glycolate, and mixtures thereof.

In certain embodiments, suitable pharmaceutically acceptable excipients may include fragrances such as, without limitations, natural and/or synthetic fragrance raw materials. For instance, oil soluble perfume oils, which may or may not be in mixture with water soluble perfume oils. Oil soluble perfume materials are natural, or natural-identical essential oils such as orange oil, lavender oil, pine oil. *eucalyptus* oil, lemon oil, clove leaf, peppermint oil, cedarwood oil, rosemary oil, bergamot oil, lavandin oil, patchouli oil, chamomile oil, jasmine oil, spike oil, rose oil. Vetiver oil, fennel oil, anise oil, thyme oil, germanium oil, menthol, and marjoram oil. An animal fragrance is for example musk, castoreum, aber or zibet. Spagyric essences are also known in the art. They are made by fermenting certain herbs that are then processed to the final product. Synthetic fragrance ingredients are for example synthetic essential oils such as composed of single compounds such as linalol, terpineol, nerol, citronellal, benzaldehyde, cinnamon aldehyde, vanillin, ethylvanillin, or methylacetophenone. The fragrance materials may also be synthetic oil soluble perfume oils selected from the usual group consisting of fragrant hydrocarbons, alcohols, ketones, aldehydes, ethers, esters, polyene derivatives. Other fragrances that may be used are catalogued and described in references and databases such as S. Arctander. Perfume and Flavor Chemicals. Volumes I and II (1960, 1969; reprint 2000); Allured's Flavor and Fragrance Materials (2005); and database maintained by the Research Institute for Fragrance Materials at www.rifm.org.

In certain embodiments, suitable pharmaceutically acceptable excipients may include a perfume oil. Suitable perfume oils include mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, *angelica*, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (*galbanum*, elemi, benzoin, myrrh, olibanum, opoponax). Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl-methylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones. α-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams.

In certain embodiments, suitable pharmaceutically acceptable excipients may include essential oils of relatively low volatility, which are mostly used as aroma components, are also suitable as perfume oils. e.g. sage oil, chamomile oil, oil of cloves, melissa oil, mint oil, cinnamon leaf oil, linden blossom oil, juniper berry oil, vetiver oil, olibanum oil. *galbanum* oil, labolanum oil and lavandin oil. Other suitable oils include bergamot oil, dihydromyrcenol, lilial, lyral, citronellol, phenylethyl alcohol. α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

In certain embodiments, suitable pharmaceutically acceptable excipients may include preservatives. The term "preservative", as used herein, refers to an agent that extends the storage life of the dosage form by retarding or preventing deterioration of flavor, odor, color, texture, appearance, therapeutic value, or safety. A preservative need not provide a lethal, irreversible action resulting in partial or complete microbial cell destruction or incapacitation. Sterilants, sanitizers, disinfectants, sporicides, viracides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act). Suitable preservatives include, without limitations, phenoxyethanol, a solution of paraben, pentanediol and sorbic acid, as well as silver complexes.

In certain embodiments, suitable pharmaceutically acceptable excipients may include coloring agents, such as, without limitations, colors such as e.g., white, black, yellow, blue, green, pink, red, orange, violet, indigo, and brown.

In certain embodiments, suitable pharmaceutically acceptable excipients may include, without limitations, "flavor extract" obtained by extracting a part of a raw material, e.g., animal or plant material, often by using a solvent such as ethanol or water; natural essences obtained by extracting essential oils from the blossoms, fruit, roots, etc., or from the whole plants. Additional exemplary flavoring agents for the compositions described herein may include, but not be limited to, menthol, spearmint, and cinnamon, coffee beans, other flavors or fragrances such as fruit flavors (e.g., cherry, orange, grape, etc.), quaternary ammonium bases. The effect of flavors may be enhanced using flavor enhancers like tartaric acid, citric acid, vanillin, or the like.

In certain embodiments, suitable pharmaceutically acceptable excipients may include sweetening agents such as, without limitations, one or more artificial sweeteners, one or more natural sweeteners, or a combination thereof. Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), stevia, chloro derivatives of sucrose such as sucralose (available as Kaltame®) and Splenda®), and mogrosides. Natural sweeteners include, e.g., glucose, dextrose, invert sugar, fructose, sucrose, glycyrrhizin; monoammonium glycyrrhizinate (sold under the trade name MagnaSweet®); *Stevia rebaudiana* (Stevioside), natural intensive sweeteners, such as Lo Han Kuo, polyols such as sorbitol, mannitol, xylitol, erythritol, and the like.

In certain embodiments, suitable pharmaceutically acceptable excipients may include alkalizing agent(s), such as, without limitations, magnesium oxide, ammonium hydroxide, sodium hydroxide, sodium carbonate, sodium citrate, trisodium phosphate and/or disodium phosphate.

In certain embodiments, suitable pharmaceutically acceptable excipients may include lubricant(s)/release agent(s) such as, but not limited to, fatty acids and their salts, fatty alcohols, fatty esters, fatty amines, fatty amine acetates and fatty amides. Other suitable lubricants may include, but not be limited to, glyceryl behenate (Compritol™ 888), metallic stearates (e.g., magnesium, calcium and sodium stearates), stearic acid, hydrogenated vegetable oils (e.g., Sterotex™), talc, waxes such as beeswax and carnauba wax, silica, fumed silica, colloidal silica, calcium stearate, long chain fatty alcohols, boric acid, sodium benzoate and sodium acetate, sodium chloride, DL-Leucine, polyethylene glycols (e.g., Carbowax™ 4000 and Carbowax™ 6000), sodium oleate, sodium benzoate, sodium acetate, sodium lauryl sulfate, sodium stearyl fumarate (Pruv™), magnesium lauryl sulfate, stearic acid, stearyl alcohol, mineral oil, paraffin, micro crystalline cellulose, glycerin, propylene glycol and combinations thereof.

In certain embodiments, suitable pharmaceutically acceptable excipients may include diluents such as, but not limited to, lactose USP, lactose USP (anhydrous), lactose USP (spray dried), starch USP, directly compressible starch, mannitol USP, sorbitol, dextrose monohydrate, microcrystalline cellulose NF, dibasic calcium phosphate dihydrate NF, sucrose-based diluents, confectioner's sugar, monobasic calcium sulfate monohydrate, calcium sulfate dihydrate NF, calcium lactate trihydrate granular NF, dextrates NF (e.g., Emdex™), dextrose (e.g., Cerelose™), inositol, hydrolyzed cereal solids such as the Maltrons™ and Mor-Rex™, amylose, powdered cellulose (e.g., Elcema™), calcium carbonate, glycine, bentonite, polyvinylpyrrolidone, and the like.

In certain embodiments, suitable pharmaceutically acceptable excipients may include oils and fats such as, but not be limited to, almond oil, argan oil, avocado oil, canola oil, cashew oil, castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, *perilla* oil, pine nut oil, pistachio oil, poppy seed oil, pumpkin seed oil, rice bran oil, safflower oil, sesame oil, shea butter, soy bean oil, sunflower oil, walnut oil, and watermelon seed oil. Other oil and fats that may be in the fill of the PVA shell may include, but not be limited to, fish oil (omega-3), crill oil, animal or vegetable fats, e.g., in their hydrogenated form, mono-, di-, and tri-glycerides with C12-, C14-, C16-, C18-, C20- and C22-fatty acids.

In certain embodiments, suitable pharmaceutically acceptable excipients may include vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxyethylcellulose, hydroxypropylcellulose, hydroxymethylcellulose, hydroxyethylmethylcellulose, hydroxypropylmethylcellulose, hydroxy butylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids, polyacrylamides, and polyacrylic acid esters, polymethacrylic acids, polymethacrylamides, and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired; and other similar polymers; inorganic fillers, such as the oxides of magnesium aluminum, silicon, titanium, etc.

In certain embodiments, suitable pharmaceutically acceptable excipients may include a hydrophobic material, including, but not limited to, digestible, long chain ($C_8$-$C_{50}$, especially $C_{12}$-$C_{40}$), substituted or unsubstituted hydrocarbons, such as natural or synthetic waxes (such as beeswax, glycowax, castor wax and carnauba wax), fatty alcohols (such as lauryl, myristyl, stearyl, cetyl or preferably cetostearyl alcohol), fatty acids, including, but not limited to, mono-diglyceride of medium chain fatty acids (such as caprylic, capric, caproic, lauric, oleic, linoleic), medium chain triglycerides, fatty acid esters, fatty acid glycerides (mono-, di-, and tri-glycerides), hydrogenated fats, hydrocarbons, normal waxes, stearic acid, stearyl alcohol and hydrophobic and hydrophilic materials having hydrocarbon backbones.

In certain embodiments, suitable pharmaceutically acceptable excipients may include polyvinyl alcohols, polyvinyl pyrrolidone, polyalkylene oxides, polyacrylic acid, cellulose, cellulose ethers, cellulose esters, cellulose amides, polyvinyl acetates, polycarboxylic acids and salts, acetic acid, caprylic acid, oleic acid, polyaminoacids or peptides, polyamides, polyacrylamide, copolymers of maleic/acrylic acids, polysaccharides including starch and gelatin, natural gums such as xanthan, and carrageenans. For example, polymers can be selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and combinations thereof, or selected from polyvinyl alcohols, polyvinyl alcohol copolymers and hydroxypropyl methyl cellulose (HPMC), methacrylic acid/ methyl methacrylate, methacrylic acid/ethyl acrylate copolymers, methacrylic acid/methyl acrylate/methyl methacrylate copolymers, shellac, hydroxypropyl methylcellulose phthalate, hydroxyl propyl methyl cellulose acetate succinate, hydroxypropyl methyl cellulose trimellitate, cellulose acetate phthalates, polyvinyl acetate phthalates, PEG-35 castor oil, caprylocaproyl polyoxyl-8 glycerides, glyceryl distearate, and combinations thereof.

In certain embodiments, suitable pharmaceutically acceptable excipients may include high HLB surfactants such as, without limitations, polysorbate 80-polyoxyethylene (20) sorbitan monooleate, polyoxyl 40 hydrogenated castor oil, polyoxyl 35 castor oil, caprylocaproyl macrogol glycerides, and combinations thereof.

In certain embodiments, suitable pharmaceutically acceptable excipients may include fillers such as, without limitations, lactose, microcrystalline cellulose, and combinations thereof.

In certain embodiments, suitable pharmaceutically acceptable excipients may include natural gums (e.g., a natural plant gum). Suitable natural gums include, without limitations, guar gum, carob gum, konjac gum, xanthan gum, *sclerotium* gum, acacia gum, cellulose gum (modified or not), or a combination thereof.

In certain embodiments, suitable pharmaceutically acceptable excipients may include emulsifiers such as, without limitations, PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60) Almond Glycerides, PEG-20 Methyl Glucose Sesquistearate, PEG-40) Stearate, PEG-100 Stearate, PEG-80 Sorbitan Laurate, Steareth-2, 1 Steareth-12, Oleth-2, Ceteth-2, Laureth-4, Oleth-10, Oleth-10/Polyoxyl 10 Oleyl Ether, Ceteth-10, Isosteareth-20, Ceteareth-20, Oleth-20, Steareth-20, Steareth-21, Ceteth-20, Isoceteth-20, Laureth-23, Steareth-100, Glyceryl Stearate Citrate, Glyceryl Stearate SE (self-emulsifying), stearic acid, salts of stearic acid, polyglyceryl-3-methylglycosedistearate, or a combination thereof.

Further suitable emulsifiers are phosphate esters and the salts thereof such as cetyl phosphate (Amphisol® A), diethanolamine cetyl phosphate (Amphisol® DEA), potassium cetyl phosphate (Amphisol® K), sodium cetearyl sulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, Cetearyl Glucoside, Lauryl Glucoside, Decyl Glucoside, Sodium Stearoyl Glutamate, Sucrose Polystearate and Hydrated Polyisobutene. Furthermore, one or more synthetic polymers may be used as an emulsifier. For example, PVP eicosene copolymer, acrylates/ $C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof.

In certain embodiments, suitable pharmaceutically acceptable excipients may include chelating agents such as, without limitations, disodium ethylenediaminetetraacetic acid (EDTA), diethylenetriaminepentaacetic acid (DTPA), N-(hydroxyethyl)-ethylenediaminetriacetic acid (HEDTA), and nitrilotriacetic acid (NTA).

In certain embodiments, suitable pharmaceutically acceptable excipients may include fatty alcohols, such as, without limitations guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of $C_{12}$-$C_{15}$ alcohols, acetylated lanolin alcohol, etc.

In certain embodiments, suitable pharmaceutically acceptable excipients may include esters of fatty acids, such as, without limitations esters of linear $C_6$-$C_{24}$ fatty acids with linear $C_3$-$C_{24}$ alcohols, esters of branched $C_6$-$C_{13}$ carboxyl acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerization of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerization of unsaturated fatty alcohols). Additional suitable examples of ester oils are isopropyl myristate, isopropyl palmitate, isopropyl stearate, isopropyl isostearate, isopropyl oleate, n-butyl stearate, n-hexyl laurate, n-decyl oleate, isooctyl stearate, iso-nonyl-stearate, isononyl isononanoate, 2-ethylhexylpalmitate, 2-hexyllaurate, 2-hexyldecylstearate, 2-octyldodecylpalmitate, olevloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

In certain embodiments, suitable pharmaceutically acceptable excipients may include other adjuvants, such as, without limitations, diethylhexyl 2,6-naphthalate, di-n-butyl adipate, di(2-ethylhexyl)-adipate, di(2-ethyl hexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups.

In certain embodiments, suitable pharmaceutically acceptable excipients may include natural or synthetic triglycerides (including glyceryl esters and derivatives), such as, without limitations, di- or triglycerides, based on Co-Cis fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow; apricot kernel oil, hazelnut oil, borage oil, etc. Additional suitable excipients include waxes including esters of long-chain acids and alcohols as well as compounds having wax-like properties, e.g., carnauba wax, beeswax (white or yellow), lanolin wax, candelilla wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

In certain embodiments, suitable pharmaceutically acceptable excipients may include pearlescent waxes, such as, without limitations, alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially lauryl and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

In certain embodiments, suitable pharmaceutically acceptable excipients may include hydrocarbon oils, such as, without limitations, mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

In certain embodiments, suitable pharmaceutically acceptable excipients may include silicones or siloxanes (organosubstituted polysiloxane), such as, without limitations, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

In certain embodiments, suitable pharmaceutically acceptable excipients may include emulsifiers, such as, without limitations, carboxylic acids and their salts: alkaline soap of sodium, potassium and ammonium, metallic soap of calcium or magnesium, organic basis soap such as Lauric, palmitic, stearic and oleic acid etc. Alkyl phosphates or phosphoric acid esters, acid phosphate, diethanolamine phosphate, potassium cetyl phosphate. Ethoxylated carboxylic acids or polyethylene glycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycol ether such as laureth-n, ceteareth-n, steareth-n, oleth-n. Fatty acid polyglycolether such as PEG-n stearate, PEG-n oleate, PEG-n cocoate. Monoglycerides and polyol esters. $C_{12}$-$C_{22}$ fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, $C_8$-$C_{22}$ alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated paraffins, sulfonated tetrapropyene sulfonate, sodium lauryl sulfates, ammonium and ethanolamine lauryl sulfates, lauryl ether sulfates, sodium laureth sulfates, sulfosuccinates, acetyl isothionates, alkanolamide sulfates, methyl taurines, taurines, imidazole sulfates. Polysiloxane/polyalkyl/polyether copolymers and derivatives, dimethicone, copolyols, silicone polyethylene oxide copolymer, silicone glycol copolymer. Propoxylated or POE-n ethers (Meroxapols). Polaxamers or poly(oxyethylene)m-block-poly(oxypropylene)n-block(oxyethylene). Zwitterionic surfactants that carry at least one quaternary ammonium group and at least one carboxylate and/or sulfonate group in the molecule. Zwitterionic surfactants that are especially suitable are betaines, such as N-alkyl-N, N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacy laminoethylhydroxyethylcarboxy methylglycinate, N-alkyl betaine, N-alkylaminobetaines. Alkylimidazolines, alkylopeptides, lipoaminoacides, self-emulsifying bases and the compounds as described in K. F. DePolo, A short textbook of cosmetology, Chapter 8, Table 8-7, p 250-251.

Suitable nonionic bases include, without limitations, PEG-6 beeswax (and) PEG-6 stearate (and) polyglyceryl-2-isostearate, glyceryl stearate (and) PEG-100 stearate, PEG-5 glyceryl stearate, sorbitan oleate (and) polyglyceryl-3 ricinoleate, sorbitan stearate and sucrose cocoate, glyceryl stearate and laureth-23, cetearyl alcohol and ceteth-20, cetearyl alcohol and polysorbate 60 and PEG-150 and stearate-20, cetearyl alcohol and cetearyl polyglucoside, cetearyl alcohol and ceteareth-20, cetearyl alcohol and PEG-40 castor oil, cetearyl alcohol and PEG-40 castor oil and sodium cetearyl sulfate, stearyl alcohol and steareth-7 and steareth-10, cetearyl alcohol and szeareth-7 and steareth-10, glyceryl stearate and PEG-75 stearate, propylene glycol ceteth-3 acetate, propylene glycol isoceth-3 acetate, cetearyl alcohol and ceteth-12 and oleth-12, PEG-6 stearate and PEG-32 stearate, PEG-6 stearate and ceteth-20 and steareth-20, PEG-6 stearate and ceteth-20 and glyceryl stearate and steareth-20, glyceryl stearate and ceteareth-20.

Suitable anionic alkaline bases includes, without limitations, PEG-2 stearate SE, glyceryl stearate SE, propylene glycol stearate. Anionic acid bases such as cetearyl Alcohol and Sodium cetearyl sulfate, cetearyl alcohol and sodium lauryl sulfate, trilaneth-4 phosphate and glycol stearate and PEG-2 stearate, glyceryl stearate and sodium lauryl Sulfate. Cationic acid bases such as cetearyl alcohol and cetrimonium bromide.

In certain embodiments, suitable pharmaceutically acceptable excipients may include adjuvants and additives, such as, without limitations, surfactants, super-fatting agents, consistency regulators, thickeners, polymers, stabilizers, biogenic active ingredients, swelling agents, further UV light-protective factors, antioxidants, hydrotropic agents, preservatives, self-tanning agents, solubilizers, perfume oils, colorants, bacteria-inhibiting agents and the like.

In certain embodiments, suitable pharmaceutically acceptable excipients may include super-fatting agents, such as, without limitations, lanolin and lecithin and also polyethoxylated or acetylated lanolin and lecithin derivatives, polyol fatty acid esters, monoglycerides and fatty acid alkanolamides, the latter simultaneously acting as foam stabilizers.

In certain embodiments, suitable pharmaceutically acceptable excipients may include surfactants, such as, without limitations, fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, .alpha.-olefin sulfonates, ethercarboxylic acids, alkyl oligoglucosides, fatty acid glucamides, alkylamidobetaines and/or protein fatty acid condensation products, the latter preferably being based on wheat proteins.

In certain embodiments, suitable pharmaceutically acceptable excipients may include consistency regulators/thickeners and rheology modifiers, such as, without limitations, silicium dioxide, magnesium silicates, aluminium silicates, polysaccharides or derivatives thereof for example hyaluronic acid, xanthan gum, guar-guar, agar-agar, alginates, carrageenan, gellan, pectines, or modified cellulose such as hydroxycellulose, hydroxypropylmethylcellulose. In addition polyacrylates or homopolymer of reticulated acrylic acids and polyacrylamides, carbomer (CARBOPOL types 980, 981, 1382, ETD 2001, ETD2020, ULTREZ 10) or SALCARE range such as SALCARE SC80 (steareth-10 allyl ether/acrylates copolymer), Salcare SC81 (acrylates copolymer), Salcare SC91 and Salcare AST (sodium acrylates copolymer/PPG-1 trideceth-6), SEPIGEL 305 (polyacry lamide/laureth-7), SIMULGEL NS and SIMULGEL EG (hydroxyethyl acrylate/sodium acryloyldimethyl taurate copolymer), STABILEN 30 (acrylates/vinyl isodecanoate crosspolymer), PEMULEN TR-1 (acrylates/$C_{10-30}$ alkyl acrylate crosspolymer), LUVIGEL EM (sodium acrylates copolymer), ACULYN 28 (acrylates/beheneth-25 methacrylate copolymer), etc.

In certain embodiments, suitable pharmaceutically acceptable excipients may include polymers, such as, without limitations, an anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylate-tert-butylaminoethyl methacry late/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatized cellulose ethers and silicones. Furthermore, the polymers as described in EP 1093796 (pages 3-8, paragraphs 17-68) may be used.

In certain embodiments, suitable pharmaceutically acceptable excipients may include antioxidants, such as, without limitations amino acids (e.g. glycine, histidine, tyrosine, tryptophan) and derivatives thereof, imidazoles (e.g. urocanic acid) and derivatives thereof, peptides, such as D,L-carnosine. D-carnosine. L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl. N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin. EDTA. EDDS. EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase. N-[3-(3,5-di-tert-butyl-4-hydroxyphenyl)propionyl]sulfanilic acid (and salts thereof, for example the disodium salts), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

In certain embodiments, suitable pharmaceutically acceptable excipients may include hydrotropic agents, such as, without limitations, ethoxylated or non-ethoxylated mono-alcohols, diols or polyols with a low number of carbon atoms or their ethers (e.g. ethanol, isopropanol, 1,2-dipropanediol, propylene glycol, glycerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows; glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

In certain embodiments, suitable pharmaceutically acceptable excipients may include preservatives, such as, without limitations, Methyl-, Ethyl-, Propyl-, Butyl-parabens, Benzalkonium chloride, 2-Bromo-2-nitro-propane-1, 3-diol, Dehydroacetic acid, Diazolidinyl Urea, 2-Dichlorobenzyl alcohol, DMDM hydantoin, Formaldehyde solution, Methyldibromoglutanitrile, Phenoxyethanol, Sodium Hydroxymethylglycinate, Imidazolidinyl Urea. Triclosan and further substance classes listed in the following reference: K. F. DePolo-A short textbook of cosmetology, Chapter 7, Table 7-2, 7-3, 7-4 and 7-5, p 210-219.

In certain embodiments, suitable pharmaceutically acceptable excipients may include bacteria-inhibiting agents, such as, without limitations, 2,4,4'-trichloro-2'-hydroxydiphenyl ether, chlorhexidine (1,6-di(4-chlorophenylbiguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2, 6,10-dodecatrien-1-ol), which is present in lime blossom oil. Glycerol monolaurate has also proved to be a bacteriostatic agent.

Other pharmaceutically acceptable excipients may also be utilized as recognized by those skilled in the art.

In certain embodiments, pharmaceutically acceptable excipients may be included (individually or cumulatively) in the pharmaceutical compositions, cosmetic compositions, cosmeceutical compositions, nutraceutical compositions, nutritional compositions described herein in a concentration ranging from any of about 5 wt %, about 10 wt %, about 15 wt %, about 20 wt %, about 25 wt %, about 30 wt %, about 35 wt %, about 40 wt %, about 45 wt %, or about 50 wt % to any of about 55 wt %, about 60 wt %, about 65 wt %, about 70 wt %, about 75 wt %, about 80 wt %, about 85 wt %, about 90 wt %, about 95 wt %, or about 99 wt %, or any sub-range or single value therein based on the total weight of the composition.

In certain embodiments, the liposomal composition provides a reduction in cellular senescence of human endothelial cells. The reduction can be in-vivo or in-vitro. In certain embodiments, the reduction of senescent cells of at least 5%, at least 10%, at least 15%, at least 20%, at least 25%, at least 30%, at least 35%, at least 40%, at least 45% or at least 50%, e.g., as compared to a control. In certain embodiments, the liposomal composition provides a reduction of senescent cells of at least 5%, at least 10%, at least 15%, at least 20%, or at least 25% as compared to a NAD+ non-liposomal compositions. In certain embodiments, the endothelial cells are human aortic endothelial cells.

In certain embodiments, the liposomal composition provides a reduction in cellular senescence of human epidermal cells. The reduction can be in-vivo or in-vitro. In certain embodiments, the reduction of senescent cells of at least 5%, at least 10%, at least 15%, at least 20%, at least 25%, at least 30%, or at least 35%, e.g., as compared to a control. In certain embodiments, the liposomal composition provides a reduction of senescent cells of at least 5%, at least 10%, or at least 15% as compared to a NAD+ non-liposomal compositions. In certain embodiments, the epidermal cells are human epidermal keratinocytes.

In certain embodiments, the liposomal composition provides an increase in cell survival of human endothelial cells.

The increase can be in-vivo or in-vitro. In certain embodiments, the increase is at least 5%, at least 10%, at least 15%, or at least 20%, e.g., as compared to a control. In certain embodiments, the liposomal composition provides an increase in cell survival of at least 25 or at least 5% as compared to a NAD+ non-liposomal compositions. In certain embodiments, the endothelial cells are human aortic endothelial cells.

In certain embodiments, the liposomal composition provides an increase in cell survival of human epidermal cells. The reduction can be in-vivo or in-vitro. In certain embodiments, the epidermal cells are human epidermal keratinocytes.

In certain embodiments, the liposomal formulations of the present invention has an increased permeability across human skin. The permeability can be in-vivo or an external model such as a perfex vivo model. In certain embodiments, the increase is at least about 135%, at least about 150%, at least about 160%, at least about 175% or at least about 190%, e.g., as measured by NCLS score against a control. In certain embodiments, the increase is at least about 10%, at least about 15%, at least about 25%, at least about 35% or at least about 50%, e.g., as measured by NCLS score against a non-liposomal formulation.

In certain embodiments, the compositions of the present invention are stored at a temperature of from about 2° C. to about 30° C., about 2° C. to about 20° C., or about 2° C. to about 10° C.

In certain embodiments, the compositions of the present invention have a temperature of from about 2° C. to about 30° C., about 2° C. to about 20° C., or about 2° C. to about 10° C.

In certain embodiments, the invention is directed to a method of distributing the formulation as described herein by transporting the product under refrigeration, e.g., by electric (e.g., refrigeration unit), chemical (e.g., by icepack such as dry ice), mechanical means (e.g., by a cooler) or combination thereof.

Stability

In certain embodiments, any of the compositions described herein exhibit long term storage stability. The term "storage stability" as described herein refers to one or more of chemical stability, physical stability, and/or microbial stability.

The term "chemical stability" refers to the evaluation of changes, e.g., decrease or increase, in the amount (or content) of active agent in the composition after a storage duration (e.g., after 1 month storage (t=1), after 3 months storage (t=3), after 6 months storage (t=6), or after 12 months storage (t=12)) as compared to the amount (or content) of the active agent before initiation of storage (t=0). A smaller change (or no change) in the amount (content) of the active agent in the composition after a given storage duration being indicative of the chemical stability of the active agent in the given composition. The chemical stability of the active agent may be analyzed with a suitable HPLC method.

In certain embodiments, any of the compositions described herein maintain more than about 90 wt %, more than about 92 wt %, more than about 94 wt %, more than about 96 wt %, more than about 98 wt %, more than about 99 wt %, or about 100 wt % of the active agent after storage at a temperature of about 2° C. to about 8° C. for a duration of about 1 month, about 3 months, about 6 months, or about 12 months, as compared to the weight of the active agent in the composition before storage (t=0).

In certain embodiments, any of the compositions described herein maintain more than about 90 wt %, more than about 92 wt %, more than about 94 wt %, more than about 96 wt %, more than about 98 wt %, more than about 99 wt %, or about 100 wt % of the active agent after storage at a temperature of about 20° C. to about 30° C. for a duration of about 1 month, about 3 months, about 6 months, or about 12 months, as compared to the weight of the active agent in the composition before storage (t=0).

In certain embodiments, any of the compositions described herein maintain more than about 90 wt %, more than about 92 wt %, more than about 94 wt %, more than about 96 wt %, more than about 98 wt %, more than about 99 wt %, or about 100 wt % of the active agent after storage at a temperature of about 35° C. to about 45° C. for a duration of about 1 month, about 3 months, about 6 months, or about 12 months, as compared to the weight of the active agent in the composition before storage (t=0).

In certain embodiments, any of the compositions described herein may exhibit any of the above described chemical stability upon storage for an extended duration (e.g., one week, two weeks, three weeks, one month, two months, three months, four months, five months, six months, seven months, eight months, nine months, ten months, eleven months, twelve months, fifteen months, eighteen months, twenty one months, or twenty four months, or any sub-range or single value therein) at a temperature ranging from about −80° C. to about 100° C., from about −50° C. to about 80° C., from about −20° C. to about 60° C., from about −5° C. to about 50° C., from 0° C. to about 45° C., from about 2° C. to about 8° C., from about 20° C. to about 30° C., from about 35° C. to about 45° C., or any sub-range or single value therein, at a relative humidity ranging from about 30% to about 50%.

The term "physical stability" refers to evaluation of change in physical properties of the composition (such as, without limitations, color, pH, viscosity, homogeneity, phase separation, and the like) after a storage duration (e.g., after 1 month storage (t=1), after 3 months storage (t=3), after 6 months storage (t=6), or after 12 months storage (t=12)) as compared to the same physical properties of the composition before initiation of storage (t=0). A smaller change (or no change) in the physical properties of the composition after a given storage duration being indicative of the physical stability of the given composition. A variety of methods may be used to analyze the physical stability of the composition, depending on the property that is being tested. For instance, a pH probe may be utilized to evaluate the pH of the composition at various time points. In another example, a viscometer may be used to evaluate the viscosity of the composition at various times.

In certain embodiments, any of the compositions described herein maintain a pH ranging from about 4 to about 9, from about 5.5 to about 8.5, or from about 6 to about 7 after storage at a temperature of about 2° C. to about 8° C. for a duration of about 1 month, about 3 months, about 6 months, or about 12 months.

In certain embodiments, any of the compositions described herein maintain a pH ranging from about 4 to about 9, from about 5.5 to about 8.5, or from about 6 to about 7 after storage at a temperature of about 20° C. to about 30° C. for a duration of about 1 month, about 3 months, about 6 months, or about 12 months.

In certain embodiments, any of the compositions described herein maintain a pH ranging from about 4 to about 9, from about 5.5 to about 8.5, or from about 6 to about 7 after storage at a temperature of about 35° C. to about 45°

C. for a duration of about 1 month, about 3 months, about 6 months, or about 12 months.

In certain embodiments, any of the compositions described herein may exhibit physical stability upon storage for an extended duration (e.g., one week, two weeks, three weeks, one month, two months, three months, four months, five months, six months, seven months, eight months, nine months, ten months, eleven months, twelve months, fifteen months, eighteen months, twenty one months, or twenty four months, or any sub-range or single value therein) at a temperature ranging from about −80° C. to about 100° C., from about −50° C. to about 80° C., from about −20° C. to about 60° C., from about −5° C. to about 50° C., from 0° C. to about 45° C., from about 2° C. to about 8° C., from about 20° C. to about 30° C., from about 35° C. to about 45° C., or any sub-range or single value therein, at a relative humidity ranging from about 30% to about 50%.

The term "microbial stability" refers to change, e.g., increase or decrease, in microbial content in the composition after a storage duration (e.g., after 1 month storage (t=1), after 3 months storage (t=3), after 6 months storage (t=6), or after 12 months storage (t=12)) as compared to the microbial content in the composition before initiation of storage (t=0). A decrease (or no change) in the microbial content of the composition after a given storage duration being indicative of the microbial stability of the given composition.

In certain embodiments, any of the compositions described herein may exhibit microbial stability upon storage for an extended duration (e.g., one week, two weeks, three weeks, one month, two months, three months, four months, five months, six months, seven months, eight months, nine months, ten months, eleven months, twelve months, fifteen months, eighteen months, twenty one months, or twenty four months, or any sub-range or single value therein) at a temperature ranging from about −80° C. to about 100° C., from about −50° C. to about 80° C., from about −20° C. to about 60° C., from about −5° C. to about 50° C., from (° C.) to about 45° C., from about 2° C. to about 8° C., from about 20° C. to about 30° C., from about 35° C. to about 45° C., or any sub-range or single value therein, at a relative humidity ranging from about 30% to about 50%.

In certain embodiments, the instant disclosure is directed to a method for stabilizing an active agent selected from nicotinic acid (NA), nicotinamide (NAM), nicotinamide mononucleotide (NMN), nicotinamide riboside (NR), nicotinamide adenine dinucleotide plus hydrogen (NADH), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+), or a mixture thereof. In one embodiment, the instant disclosure is directed to a method for stabilizing NAD+.

In certain embodiments, the method includes encapsulating any of the active agents described hereinabove (such as, without limitations, NAD+) in a liposome. In certain embodiments, encapsulating any of the active agents described hereinabove (such as, without limitations, NAD+) in a liposome provides for a liposomal composition which exhibits long term storage stability at various temperatures. In certain embodiments, long term refers to a term ranging from any of about one week, about two weeks, about three weeks, about one month, about two months, about three months, about four months, about five months, or about six months to any of about seven months, about eight months, about nine months, about ten months, about eleven months, about twelve months, about fifteen months, about eighteen months, about twenty one months, or about twenty four months, or any sub-range or single value therein. In certain embodiments, storage stability refers to one or more of chemical stability, physical stability, and/or microbial stability. In certain embodiments, various temperatures refers to a temperature ranging from about −80° C. to about 100° C., from about −50° C. to about 80° C., from about −20° C. to about 60° C., from about −5° C. to about 50° C., from 0)° C to about 45° C., from about 2° C. to about 8° C., from about 20° C. to about 30° C., from about 35° C. to about 45° C., or any sub-range or single value therein.

Method of Preparation

In certain embodiments, the instant disclosure is directed to a method of preparing any of the compositions described herein. In certain embodiments, the method includes forming a solution that includes an active agent and a solvent.

In certain embodiments, the active agent may be selected from nicotinic acid (NA), nicotinamide (NAM), nicotinamide mononucleotide (NMN), nicotinamide riboside (NR), nicotinamide adenine dinucleotide plus hydrogen (NADH), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+), or a mixture thereof. In one embodiment, the active agent may be NAD+.

In certain embodiments, the solvent may include, without limitations, an alcohol, water, or a mixture thereof. In certain embodiments, the solvent includes an alcohol selected from ethanol, isopropanol, propylene glycol, glycerol, ethylene glycol, ethylene glycol monoethyl, monobutyl ether, propylene glycol monomethyl, propylene glycol monoethyl ether, propylene glycol monobutyl ether, diethylene glycol monomethyl, diethylene glycol monomethyl ether, diethylene glycol monoethyl ether, butylene glycol, pentylene glycol, sorbitol, or a mixture thereof. In certain embodiments, the solvent includes water, glycerol, and pentylene glycol.

In certain embodiments, forming a solution that includes an active agent and a solvent comprises mixing the active agent with a first solvent, optionally adding a pH adjusting agent, followed by adding a second solvent. In an exemplary embodiment, the active agent is mixed with a solution of glycerin in water, followed by addition of a pH adjusting agent (e.g., sodium hydroxide), followed by addition of pentylene glycol.

In certain embodiments, the method may further include combining (e.g., adding and mixing) a liposome matrix into the active agent solution to encapsulate the active agent into the liposome. In certain embodiments, the liposome matrix may include any of the previously described vesicle forming lipids (such as, without limitations, lecithin), one or more of the previously described solvents (such as, without limitations glycerin, water, pentylene glycol, or a mixture thereof), optionally a pH adjusting agent (such as, without limitations sodium hydroxide), and optionally an antioxidant (such as, without limitations, tocopherol).

In certain embodiments, the method further includes adjusting the pH of the composition by adding a pH adjusting agent (such as sodium hydroxide).

In certain embodiments, the instant disclosure may be directed to a method of preparing a pharmaceutical composition, a cosmetic composition, a cosmeceutical composition, a nutraceutical composition, or a nutritional composition. The term "pharmaceutical composition" refers to a composition manufactured for use for medicinal purposes. The term "cosmeceutical composition" refers to a cosmetic composition scientifically proven to have medicinal properties. The term "cosmetic composition" refers to a composition refers to a composition that can maintain, protect, clean, add fragrance, change appearance, and the like without penetrating the skin or changing the functioning of the skin. The term "nutraceutical composition" refers to a composition which other than nutrition may also be used for medicinal purposes. The term "nutritional composition" refers to a supplement intended to supplement a subject's diet by providing additional nutrients.

In certain embodiments, any of these compositions may be prepared by combining active agent encapsulated in the liposome with one or more additional pharmaceutically acceptable excipients suitable (such as those detailed hereinabove or understood by those skilled in the art) for forming a certain composition (e.g., pharmaceutical composition, a cosmetic composition, a cosmeceutical composition, a nutraceutical composition, or a nutritional composition).

In certain embodiments, the instant disclosure may be directed to a method of preparing a topical composition by combining an active agent encapsulated in a liposome with one or more additional pharmaceutically acceptable excipients suitable, wherein the active agent is selected from nicotinic acid (NA), nicotinamide (NAM), nicotinamide mononucleotide (NMN), nicotinamide riboside (NR), nicotinamide adenine dinucleotide plus hydrogen (NADH), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+), or a mixture thereof, preferably wherein the active agent is NAD+.

Exemplary topical compositions may be in a form of a serum, emulsion, cream, foam, spray, ointment, gel, lotion, or as a pad or roll-on applied formulation. Other suitable forms of a topical composition, as understood by those skilled in the art, are also contemplated herein.

In certain embodiments, the instant disclosure may be directed to a method of preparing an oral composition by combining an active agent encapsulated in a liposome with one or more additional pharmaceutically acceptable excipients suitable, wherein the active agent is selected from nicotinic acid (NA), nicotinamide (NAM), nicotinamide mononucleotide (NMN), nicotinamide riboside (NR), nicotinamide adenine dinucleotide plus hydrogen (NADH), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+), or a mixture thereof, preferably wherein the active agent is NAD+.

Exemplary oral compositions may be in a form of tablet, a capsule, caplets, a lozenge, a troche, a chewable tablet, a gum, a gummy, a syrup, a liquid solution, a suspension, an emulsion, a buccal film, a sublingual film, an oral adhesive film, a powder, solid crystals, an orally-disintegrating tablet, a paste, an oral cream, an oral gel, or an oral ointment. Other suitable forms of oral compositions, as understood by those skilled in the art, are also contemplated herein.

In certain embodiments, the instant disclosure may be directed to a method of preparing a parenteral composition by combining an active agent encapsulated in a liposome with one or more additional pharmaceutically acceptable excipients suitable, wherein the active agent is selected from nicotinic acid (NA), nicotinamide (NAM), nicotinamide mononucleotide (NMN), nicotinamide riboside (NR), nicotinamide adenine dinucleotide plus hydrogen (NADH), nicotinamide adenine dinucleotide phosphate (NADP), nicotinic acid adenine dinucleotide phosphate (NAADP), nicotinamide adenine dinucleotide phosphate (NADPH), nicotinamide adenine dinucleotide (NAD+), or a mixture thereof, preferably wherein the active agent is NAD+.

The various compositions described herein may be formulated to have a customized release profile for the active agent, such as, without limitations, an immediate release profile, a controlled release profile, a delayed release profile, an enteric release profile, a zero order release profile, a first order release profile, a pulsatile release profile, a targeted release in a certain location within the body (such as a target location within the gastrointestinal tract), and the like.

Method of Treatment

In certain embodiments, the instant disclosure is directed to a method of treating a condition in a subject by administering any of the compositions described herein (which include a liposome encapsulating NAD, a precursor thereof, a derivative thereof, or a mixture thereof, and preferably NAD+) to a subject in need thereof. The administration may be oral administration of an oral composition, topical administration of a topical composition, or parenteral administration of an injectable composition.

In certain embodiments, subjects that may be treated for one or more of loss of skin firmness, decrease of skin thickness, fine lines, wrinkles, loss of elasticity, sagging, dryness, age spots, diminished rate of turnover, abnormal desquamation, decrease of the density and disorganization of the extra-cellular matrix in the dermis and other histological changes, skin roughness, skin smoothness, brightness, radiance, UV damage, free radical damage, radiation damage, pollution damage, damage from environmental toxins or irritants or allergans, skin tone, weather-beaten appearance, yellowing, skin pores becoming less noticeable, hyperpigmentation, scars, skin surface irregularities, rosacea, exogenous eczema, acne, psoriasis, skin's regenerative and renewal process, redness, ichthyosis, lack of tactile smoothness, lack of visual smoothness, lack of softness, lack of luminosity, lack of radiance, skin texture, crow's feet, nasal fold, dyschromia, crepey skin texture, reduction in skin elasticity, and other damaging skin conditions.

In certain embodiments, the subject may be treated for one or more of fatigue (e.g., chronic fatigue syndrome), neurocognitive difficulties, sleep disturbance, postexertional malaise, headaches, muscle weakness, arthralgia, myalgias, allergy, swelling and tenderness of lymph nodes, depression, and other stress related conditions or conditions that could benefit from regulating cellular energy metabolism.

In certain embodiments, the method may include administering any of the compositions described herein regularly for a duration ranging from about 1 week to about 52 weeks, about 2 weeks to about 40 weeks, about 4 weeks to about 20 weeks, about 8 to about 16 weeks, or any single value or sub-range therein. In certain embodiments, the method may include administering any of the compositions described herein regularly for a duration of at least 1 week, at least 2 weeks, at least 4 weeks, at least 8 weeks, at least 12 weeks, at least 16 weeks, at least 20 weeks, or at least 24 weeks. In certain embodiments, the method may include administering any of the compositions described herein regularly for a duration of up to 10 years, up to 8 years, up to 5 years, up to 3 years, up to 2 years, up to 1 year, up to 9 months, up to 6 months, or up to 3 months.

In certain embodiments, administration may range from once a month to 4 times a day, from once every two weeks to twice daily, or from once a week to once daily, or any single value or sub-range therein (such as, without limitations, twice daily, thrice daily, once every two days, once every three days, etc).

In certain embodiments, regular administration of the compositions described herein exhibit an actual or perceived improvement in one or more of loss of skin firmness, decrease of skin thickness, fine lines, wrinkles, loss of elasticity, sagging, dryness, age spots, diminished rate of turnover, abnormal desquamation, decrease of the density and disorganization of the extra-cellular matrix in the dermis and other histological changes, skin roughness, skin smoothness, brightness, radiance, UV damage, free radical damage, radiation damage, pollution damage, damage from environmental toxins or irritants or allergans, skin tone, weather-beaten appearance, yellowing, skin pores becoming less noticeable, hyperpigmentation, scars, skin surface irregularities, rosacea, exogenous eczema, acne, psoriasis, skin's regenerative and renewal process, redness, ichthyosis, lack of tactile smoothness, lack of visual smoothness, lack of softness, lack of luminosity, lack of radiance, skin texture, crow's feet, nasal fold, dyschromia, crepey skin texture, reduction in skin elasticity, and other damaging skin conditions.

In certain embodiments, regular administration of the compositions described herein exhibit an actual or perceived improvement in one or more of fatigue (e.g., chronic fatigue syndrome), neurocognitive difficulties, sleep disturbance, postexertional malaise, headaches, muscle weakness, arthralgia, myalgias, allergy, swelling and tenderness of lymph nodes, depression, and other stress related conditions or conditions that could benefit from regulating cellular energy metabolism.

In certain embodiments administering a topical composition includes applying the topical composition to a patient's skin surface. The terms "application," "apply," and "applying" with respect to a disclosed topical composition, or method of using a disclosed topical composition, refer to any manner of administering a topical composition to the skin of a patient which, in medical or cosmetology practice, delivers the composition to the patient's skin surface. Smearing, rubbing, spreading, spraying a disclosed topical composition, with or without the aid of suitable devices, on a patient's skin are all included within the scope of the term "application," as used herein. The terms "topical" or "topically" with respect to administration or application of a disclosed formulation refer to epicutaneous administration or application, or administration onto skin.

In certain embodiments administering an oral composition includes ingesting the oral composition, inhaling the oral composition, applying the oral composition in the oral cavity of a patient, or placing the oral composition in the oral cavity of a patient.

In certain embodiments administering a parenteral composition to a patient includes injecting the composition to the patient's muscle (intramuscular administration), to the patient's vein (intravenous administration), or under the patient's skin (subcutaneous administration).

ILLUSTRATIVE EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1—Liposomal Concentrate of NAD+ in Glycerin/Water, Preservative-Free, Self-Preserving Liposomal concentrate of NAD+ in glycerin/water, according to embodiments of the instant disclosure, was prepared in Batch Preparation 1. Batch Preparation 1 had the concentrations indicated in the Table below.

| | Batch Preparation 1 Composition | | | |
|---|---|---|---|---|
| | CAS | EINECS | Concentration (wt %) | |
| Component | No. | No. | Preparation 1 | Preparation 2 |
| Glycerin | 56-81-5 | 200-289-5 | ad 100% | 62% |
| Water | 7732-18-5 | 231-791-2 | 22.9% | 22% |
| Nicotinamide Adenine Dinucleotide | 53-84-9 | 200-184-4 | 5.0% | 5.0% |
| Pentylene Glycol | 5343-92-0 | 226-285-3 | 4.7% | 5.0% |
| Lecithin | 8030-76-0 | 310-129-7 | 4.0% | 5.0% |
| | 8002-43-5 | 232-307-2 | | |
| Sodium Hydroxide | 1310-73-2 | 215-185-5 | 0.3% | <1% |
| Tocopherol | 1406-66-2 | 604-195-9 | 0.020% | <0.1% |

Batch Preparation 1 had a fluid appearance and a beige turbid color. The pH value of Batch Preparation 1 at 25° C. ranged from 5.5-7 (per SOP method 0009), the density (per SOP method 0007) at 20° C. was 1.175-1.195 g/cm$^3$, the refractive index (per SOP method 0008) at 20° C. was 1.435-1.455, a water content (per SOP method 0025) ranging from 21.0-25.0 wt %. When the solubility of a sample from Batch Preparation 1 was assessed in 10% water, the solution was cloudy. When the solubility of a sample from Batch Preparation 1 was assessed in IPA, it precipitated. The aerobic mesophilic bacteria of Batch Preparation 1 (per SOP method 0216) was maximum 100 cfu/g. The yeast and mold of Batch Preparation 1 (per SOP method 0217) was maximum 50 cfu/g. The *E. coli* of Batch Preparation 1 (per SOP method 0254) was negative.

A 100 kg batch, referred to as "Batch Preparation 1" (with a composition outlined as Preparation 2 in the above table), was prepared according to the process detailed below.

All ingredients/components were pre-cooled. Thereafter, 68.8 kg of an 85% glycerin solution was charged into a stirred tank, followed by addition of 5.0 kg of NAD+, followed by mixing for 15 minutes, followed by addition of 3.0 kg of a 10% NaOH solution, followed by short mixing, followed by addition of 3.0 kg of pentyleneglycol, followed by short mixing, followed by addition of 20.0 kg of Natipide™ Eco, followed by 15 minute mixing, followed by adjusting of the pH with NaOH to a pH of 6.5. Batch Preparation 1 was stored at 2-8° C. until initiation of the stability study.

Example 2—Stability Study

Three Batch preparations are prepared as follows:
Batch Preparation 1—Liposome (5% NAD+ in glycerin+water) prepared according to Example 1
Batch Preparation 2—a mixture of 5% NAD+ in glycerin+water without formation of a liposome
Batch Preparation 3—5% NAD+ in water with a preservative (0.15% potassium sorbate and 0.3% sodium benzoate), pH adjusted to 4.2 with NaOH, and without any additional components Samples from each Batch preparation are stored at the following temperatures:

Fridge at 4° C.-8° C.

Room Temperature (RT) at about 21° C.-25° C.

Oven at about 40° C.

Samples from each Batch preparation at each of the temperatures are analyzed after the following storage duration time points:

- $T = 0$ (before storage initiation)
- $T = 1$ (after one month of storage)
- $T = 3$ (after three months of storage)
- $T = 6$ (after six months of storage)
- $T = 12$ (after twelve months of storage)

The stability study is performed without humidity control and the humidity at the various storage conditions ranged from about 30% to about 50%.

At each time point, the samples are analyzed to evaluate their chemical stability by measuring the NAD+ assay (content) against baseline specifications. The measurement of the NAD+ content was done with a customized HPLC method. At each time point, the samples are analyzed to evaluate their physical stability by evaluating properties, such as, one or more of appearance, color, odor, and pH.

Stability Study Results—Batch Preparation 1
(Liposome (5% NAD+ in glycerin + water))

| Tests | T = 0 | T = 1 | T = 3 | T = 6 | T = 12 |
|---|---|---|---|---|---|
| NAD+ Assay 6° C. | 5.1% | 4.9% | 4.9% | 4.7% | |
| NAD+ Assay RT | 5.1% | 4.3% | 2.9% | 1.2% | |
| NAD+ Assay 40° C. | 5.1% | 0.9% | 0.0% | | |

Stability Study Results—Batch Preparation 2
(a mixture of 5% NAD+ in glycerin + water; no liposome)

| Tests | T = 0 | T = 1 | T = 3 | T = 6 | T = 12 |
|---|---|---|---|---|---|
| NAD+ Assay 6° C. | 5.2% | 5.1% | 5.1% | 4.8% | |
| NAD+ Assay RT | 5.2% | 4.3% | 2.9% | 1.2% | |
| NAD+ Assay 40° C. | 5.2% | 0.8% | 0.0% | na | na |

Stability Study Results—Batch Preparation 3
(5% NAD+ in water with a preservative)

| Tests | T = 0 | T = 1 | T = 3 | T = 6 | T = 12 |
|---|---|---|---|---|---|
| NAD+ Assay 6° C. | 5.2% | 5.0% | 5.0% | 4.7% | |
| NAD+ Assay RT | 5.2% | 4.4% | 3.2% | 1.6% | |
| NAD+ Assay 40° C. | 5.2% | 1.3% | 0.1% | na | |

Physical properties of Batch Preparation 1 at 6° C., RT, and 40° C. were also analyzed at T=0, T=1, T=3, T=6, and T=12. The results are summarized in the Table below.

| Tests | | T = 0 | T = 1 | T = 3 | T = 6 | T = 12 |
|---|---|---|---|---|---|---|
| Physical Properties - Batch Preparation 1 (Liposome (5% NAD+ in glycerin + water)) - 6° C. storage | | | | | | |
| Appearance | Color | characteristic | characteristic | characteristic | characteristic | |
| | Odor | characteristic | characteristic | characteristic | characteristic | |
| pH (value at 25° C.) | | 6.4 | 6.0 | 5.1 | 5.1 | |
| Density (value at 20° C.) (g/cm³) | | 1.190 | 1.190 | 1.190 | 1.190 | |
| Refractive Index (value at 20° C.) | | 1.446 | 1.445 | 1.445 | 1.445 | |
| Water content | | 22.7% | 22.5% | 22.3% | 22.8% | |
| Solubility 10% in water | | characteristic | characteristic | characteristic | characteristic | |
| Solubility 10% in IPA | | characteristic | characteristic | characteristic | characteristic | |
| Aerobic mesophilic bacteria (cfu/g) | | <10 cfu/g | <10 cfu/g | <10 cfu/g | <10 cfu/g | |
| Yeasts & Mold (cfu/g) | | <10 cfu/g | <10 cfu/g | <10 cfu/g | <10 cfu/g | |
| *Escherichia Coli* | | Negative | Negative | Negative | Negative | |
| Physical Properties - Batch Preparation 1 (Liposome (5% NAD+ in glycerin + water)) - RT storage | | | | | | |
| Appearance | Color | characteristic | characteristic | characteristic | characteristic | |
| | Odor | characteristic | characteristic | characteristic | characteristic | |
| pH (value at 25° C.) | | 6.4 | 4.7 | 4.1 | 4.1 | |
| Density (value at 20° C.) (g/cm³) | | 1.190 | 1.191 | 1.190 | 1.199 | |
| Refractive Index (value at 20° C.) | | 1.446 | 1.445 | 1.445 | 1.445 | |
| Water content | | 22.7% | 22.8% | 22.2% | 22.8% | |
| Solubility 10% in water | | characteristic | characteristic | characteristic | characteristic | |
| Solubility 10% in IPA | | characteristic | characteristic | characteristic | characteristic | |
| Aerobic mesophilic bacteria (cfu/g) | | <10 cfu/g | <10 cfu/g | <10 cfu/g | <10 cfu/g | |
| Yeasts & Mold (cfu/g) | | <10 cfu/g | <10 cfu/g | <10 cfu/g | <10 cfu/g | |
| *Escherichia Coli* | | Negative | Negative | Negative | Negative | |

| Tests | | T = 0 | T = 1 | T = 3 | T = 6 | T = 12 |
|---|---|---|---|---|---|---|
| Physical Properties - Batch Preparation 1 (Liposome (5% NAD+ in glycerin + water)) - 40° C. storage | | | | | | |
| Appearance | Color | characteristic | characteristic | characteristic | | |
| | Odor | characteristic | characteristic | characteristic | | |
| pH (value at 25° C.) | | 6.4 | 3.8 | 3.6 | | |
| Density (value at 20° C.) (g/cm³) | | 1.190 | 1.189 | 1.203 | | |
| Refractive Index (value at 20° C.) | | 1.446 | 1.445 | 1.445 | | |
| Water content | | 22.7% | 22.4% | 22.2% | | |
| Solubility 10% in water | | characteristic | characteristic | characteristic | | |
| Solubility 10% in IPA | | characteristic | characteristic | characteristic | | |
| Aerobic mesophilic bactera (cfu/g) | | <10 cfu/g | <10 cfu/g | <10 cfu/g | | |
| Yeasts & Mold (cfu/g) | | <10 cfu/g | <10 cfu/g | <10 cfu/g | | |
| *Escherichia Coli* | | Negative | Negative | Negative | | |

It found that Batch 1 had similar data as Batch 2 even though the active was subject to exposure to additional excipient and possibility of degradation due to the liposomal preparation. Further, it was found that for optimal stability, NAD+ should be kept cold, e.g., at about 6° C. This is worth noting because cosmetic products on the market that include NAD+ are not handled and stored in the cold. Rather, these cosmetic products are stored at room temperature.

An additional test was conducted to check the formulations for the NAD+ liposome content at different concentrations and varying temperatures. From this test, it could assure that the final cosmetic product can be kept over a longer time.

Formulation 1 was prepared such that the NAD+ liposome content was 1%. Formulation 2 was prepared such that the NAD+ liposome content was 5%. The amount of NAD+ liposome was measured at different time points. The results are presented in the Table below.

| Concentration Study Results—Formulation 1 (1% NAD+ liposome) | | | | | |
|---|---|---|---|---|---|
| Tests | T = 0 | T = 2 weeks | T = 1 month | T = 3 months | T = 6 months |
| NAD+ Assay 6° C. | 0.054% | 0.054% | 0.050% | 0.050% | 0.050% |
| NAD+ Assay RT | 0.54% | 0.053% | 0.049% | 0.040% | 0.039% |
| NAD+ Assay 40° C. | 0.054% | 0.031% | 0.015% | 0.001% | n.d. |
| Concentration Study Results—Formulation 2 (5% NAD+ liposome) | | | | | |
| Tests | T = 0 | T = 1 week | T = 2 weeks | T = 3 weeks | T = 1 month |
| NAD+ Assay 6° C. | 0.23% | 0.22% | 0.21% | 0.21% | 0.21% |
| NAD+ Assay RT | 0.23% | 0.22% | 0.21% | 0.21% | 0.20% |
| NAD+ Assay 40° C. | 0.23% | 0.17% | 0.12% | 0.08% | 0.06% |

From this study, it was found that formulations having 1% and 5% had similar results for stability at 6° C. and room temperature, where both were stable for a minimum of 3 months at 20° C. and 6 months at 6° C.

Permeability Study

A permeability study was performed to evaluate penetration of two formulations through human skin by infrared spectroscopy using frozen human skin explants Perfex vivo. Formulation A was prepared using a 5% NAD+ in glycerin and water without liposome and Formulation B was prepared using a 5% NAD+ liposome concentrate.

The study was designed to be performed in three consecutive stages. In Stage 1, a feasibility study was conducted. During the feasibility study, the spectral signatures of Formulation A and B were determined to be sure that it is possible to detect the peaks, specific for analyzed molecules by infrared assay. If the results are negative, then the study ends. In Stage 2, a preliminary test was conducted to test penetration of the formulations through human skin Perfex vivo after 24 hours. If the formulations are not detectable in the skin, the study ends. In Stage 3, a complete penetration test is performed.

The two formulations tested are presented below. In formulation A, NAD+ is at 5% concentration. The formulations were stored at 4° C. before, within and after the period of the study.

| Formulation | Identification | Reference | Batch | Aspect |
|---|---|---|---|---|
| A (P1) | NAD + | 740103.00.0 | 4648 4600 | Powder |
| B (P2) | NAD + liposome | 410240.00.2 | 119 572 | Opaque liquid |

To prepare formulation A for testing, it was dissolved at 5% in sterile distillate water. Formulation B was tested in its pure form.

To prepare the Perfex vivo explants, 13 circular skin explants of 38 mm in diameter were prepared from an abdoplasty coming from a 29 year old Caucasian woman (reference: P2389-AB29) with a type II phototype, without stretch mark and without hair. The explants were held on a specifically designed support composed of a reservoir of culture medium surmounted by a grid on which the skin is stretched. The skin support was connected by a fluidic circuit to a second reservoir of culture medium which was stored in the incubator at 37° C. (high RH %+5% $CO_2$. The circulation of the culture medium was ensured by a peristaltic pump.

The Perfex vivo explants were distributed into 3 batches as follows:

| Batch | Designation | Treatment | Number of explants | Sampling Time |
|---|---|---|---|---|
| T | Untreated control | / | 1 | Day 1 (T24 h) |
| P1 | Formulation A at 5% in sterile distillate water | P1 | 1 | Day 1 (T24 h) |
| P2 | Formulation B at 100% pure | B | 1 | Day 1 (T24 h) |

*Due to the large diameter of Perfex vivo explants, the skin samplings are divided into 3 replicates for each explant.

On day 0 (D0), the tested products P1 and P2 were applied topically on the basis of 9 μL per explant (2 μL/cm$^2$) and spread using a small spatula. The control T did not receive any treatment.

On D1, the 3 explants form the batch T0 were collected and cut into three parts. One quarter was fixed in buffered formalin solution and one quarter was frozen at −80° C. for histological analysis, and the half was kept at −80° C. and sent for Raman spectroscopy analysis. On D1, 3 explants from the concerned batches were collected and treated in the same way than in D0. On D1, the explants of each batch have been sampled. Each Perfex vivo explant is frozen at −80° C. Each explant was successively sectioned in six parts. Three parts were stored at −80° C. and three parts were frozen at −80° C. for cryo-sectioning, as indicated in FIG. 1

Sections of the explants were prepared for histological processing. To prepare this sections, 10 μm thick sections were made using a Leica RM 2125 Minot-type microtome, and the sections were mounted on a CaF$_2$ specific support for infrared spectroscopy imaging analysis.

Infrared of acquisition parameters was also performed. To optimize the acquisition parameters, data collection was performed with a spotlight 400 (Perkin Elmer). Different acquisition parameters were tested to adapt to the studied skin sections:

Spectral range: 750-4000 cm-1
Spectral resolution: 4 cm$^{-1}$ spectral resolution
Pixel size (spatial resolution): 6.25*6.25 μm2
Average number of spectra in hyperspectral image 15000 spectra
Average surface of hyperspectral images: 500,000 μm2 (0.5 mm2)
Average acquisition time per hyperspectral FTIR image: 12 hours Six reference spectra were collected for the formulation P1 and P2. FTIR signal preprocessing and processing was also performed. Classical data preprocessing (atmospheric correction, signal to noise evaluation, smoothing, baseline correction and normalization) was performed.

Atmospheric correction enabled to eliminate the contribution of the atmospheric H$_2$O and CO$_2$ in from each spectrum in the spectral images Signal to noise evaluation enabled to eliminate the collected spectra from outside the skin sections Smoothing consisted on a four-degree polynomial Savitzky-Golay algorithm with a window of 12 points Baseline removal: baseline was corrected using a polynomial function Normalization: all spectra were normalized based on the integrated AUC of the CH stretching band between 2800 and 3000 cm-1

Matlab (Matworks) was used and in-house data processing procedures were developed for this study. Both univariate and multivariate data analyses were applied in order to detect and follow "P1" and "P2" in the epidermis. For semi quantitative evaluation, all data were extracted for hyperspectral images and values from zones of interest were averaged and standard deviations were calculated. In this study, "SD" refers to standard deviation, "D" and "J" refer to day. It is noted that "J" represents "Jours," which is the French word for day used in the Figures.

Figure 2:
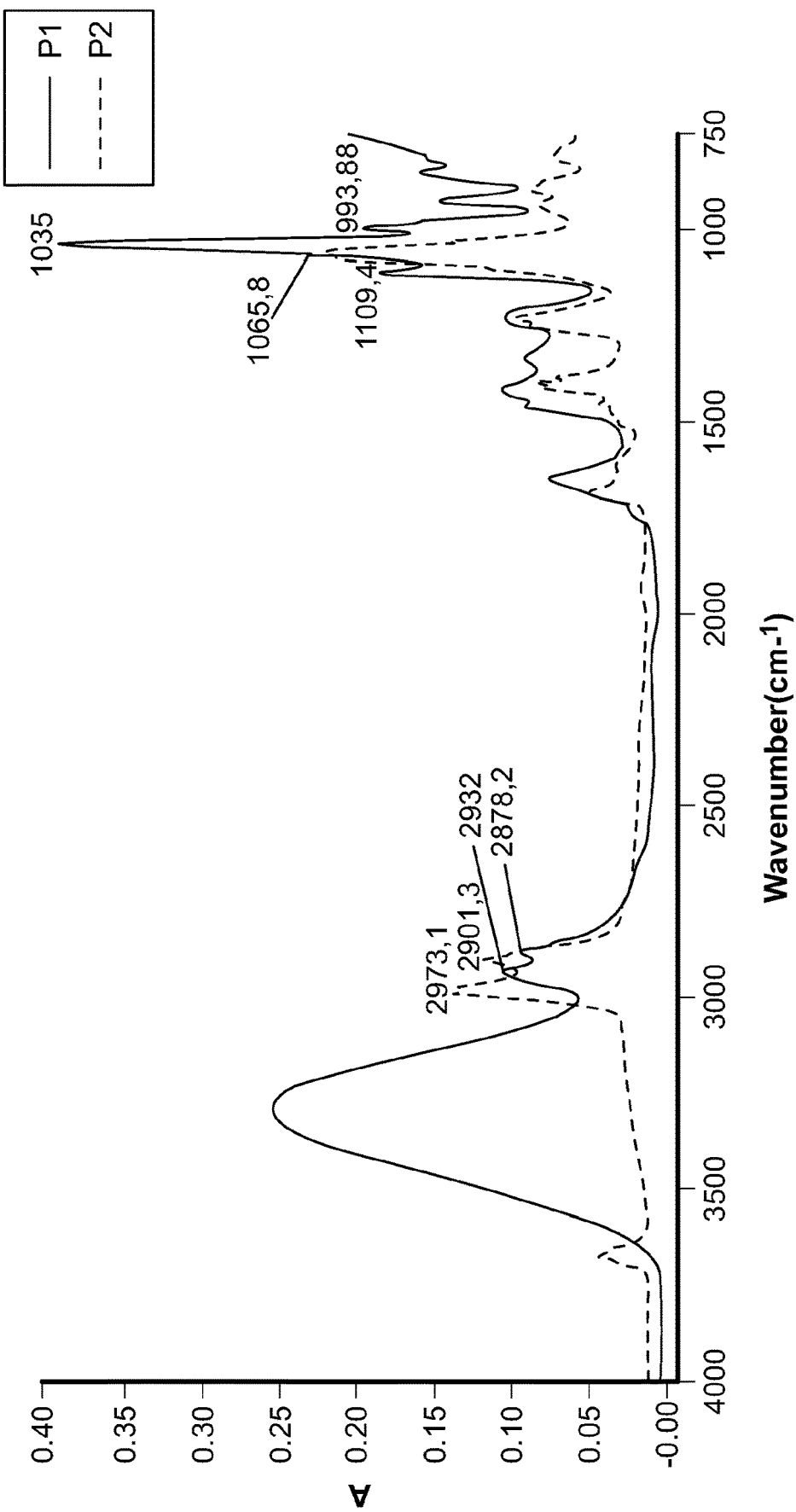
FIG. 2 is an FTIR spectrum of the formulation P1 and P2.

Stage 1: The formulation P1 and P2 were analyzed by infrared spectroscopy in order to determine their molecular signature and determine the chemical tracers (peaks) to be used to follow the penetration across the skin. FIG. 2 is an FTIR spectrum of the formulation P1 and P2. In FIG. 2, the band at approximately 1030 cm$^{-1}$ presents the highest intensity in the active ingredient spectrum and was selected in order to follow the product penetration into the skin. When observing the spectra in FIG. 2, one can observe that both the active ingredient and liposomes have a contribution in the high wavenumber region. The product "P2" presents the spectral band at 2930 cm$^{-1}$ and as a consequence potentially associated to liposomes. This peak was also used in order to follow the product penetration into the skin.

Figure 3:
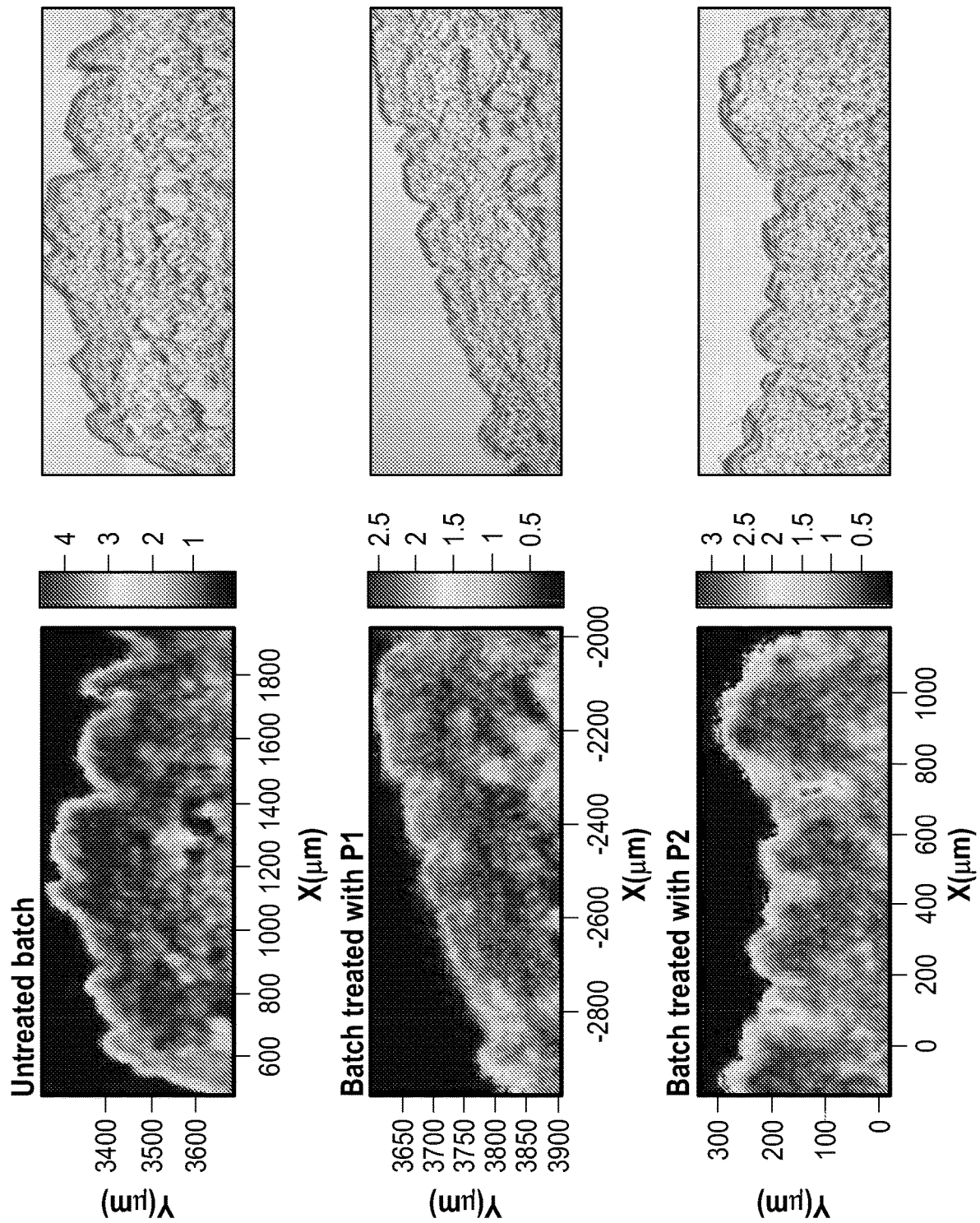
FIG. 3 are FTIR chemical images representing the variation of the AUC of the band around 1030 $cm^{-1}$ for the batches TJ1, P1J1 and P2J1.

Stage 2 and 3: Analysis of 1030 cm$^{-1}$ band was performed. FTIR chemical images representing the variation of the AUC of the band around 1030 cm$^{-1}$ for the batches TJ1, P1J1 and P2J1 are presented in FIG. 3. On Day 1, on the control batch, a very slight signal on both stratum corneum and epidermis for the band at 1030 cm$^{-1}$ was detected. On the batch P1J1, a slight signal of the band around 1030 cm$^{-1}$ was observed in the stratum corneum and very slightly was observed in the epidermis. On the batch P2J1, a fairly clear signal of the band around cm$^{-1}$ was observed in the stratum corneum and a moderate signal was observed in the epidermis.

Figure 4:
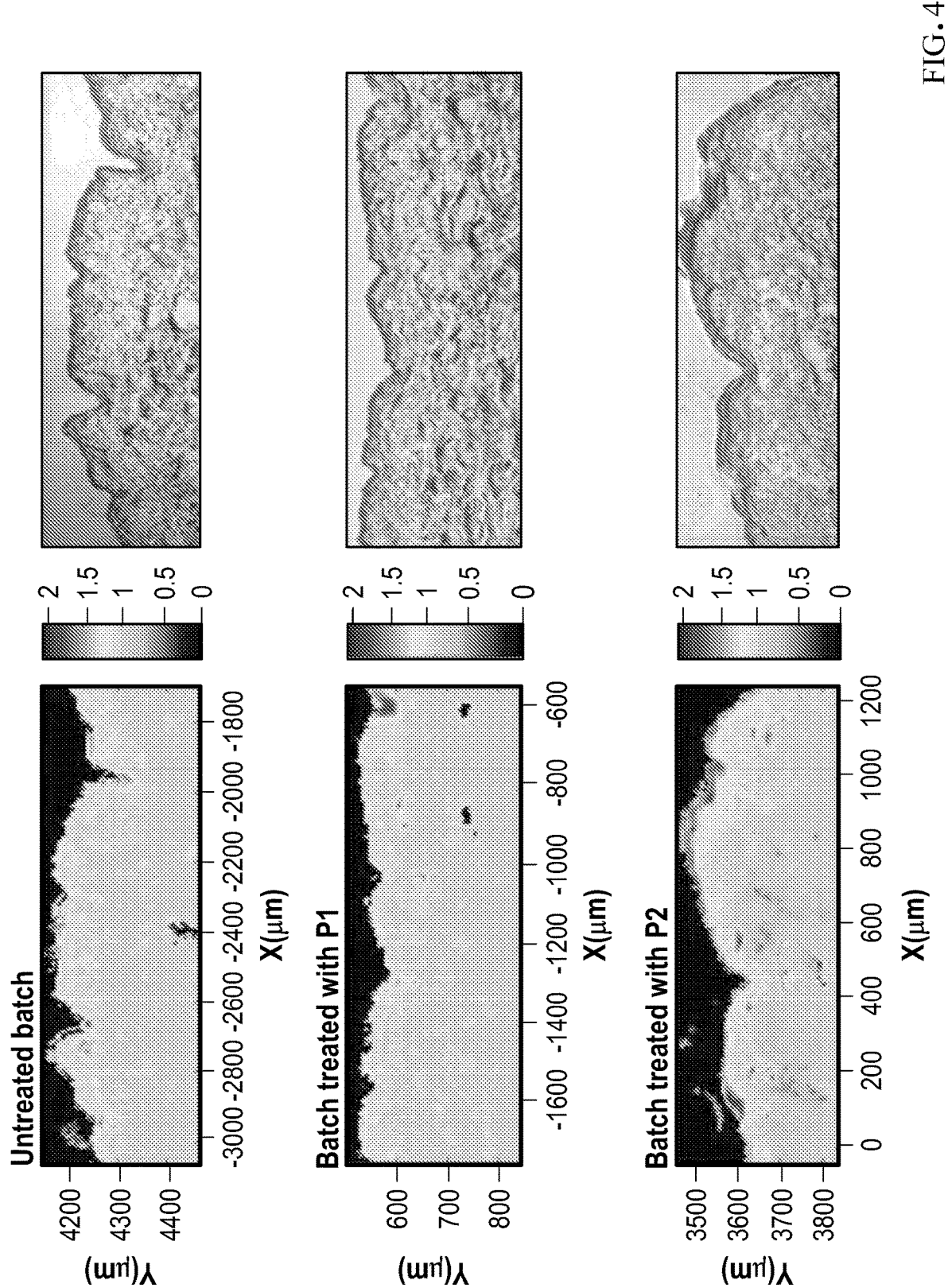
FIG. 4 are FTIR chemical images representing the variation of the 2930/2960 $cm^{-1}$ ratio.

Analysis of 2930 cm$^{-1}$ band was also performed. The CH$_2$ stretching band (2930 cm$^{-1}$) is regularly used as lipids descriptor and CH$_3$ stretching bands (2960 cm-1) as proteins descriptors. Since the formulation P2 shows the spectral band at 2930 cm$^{-1}$ the ratio 2930/2960 cm$^{-1}$, which is generally used to follow the lipids to proteins ratio, was used in the study to detect the contribution of the active ingredient and liposomes in each pixel of the hyperspectral images. Chemical images representing the variation of the 2930/2960 cm$^{-1}$ ratio are shown in FIG. 4. Due to the high content of lipids in the stratum corneum, the analysis of 2930/2960 cm$^{-1}$ ratio is realized only in the viable epidermis and the papillary dermis. On Day 1 on the control TJ1, the ratio 2930/2960 cm$^{-1}$ was weak in the epidermis and very weak in the papillary dermis. On Day 1 on the batch P1J1, the ratio 2930/2960 cm$^{-1}$ was weak in the epidermis and very weak in the papillary dermis. On Day 1 on the batch P2J2, the ratio 2930/2960 cm$^{-1}$ was moderate in the epidermis and weak in the papillary dermis.

Figure 5:
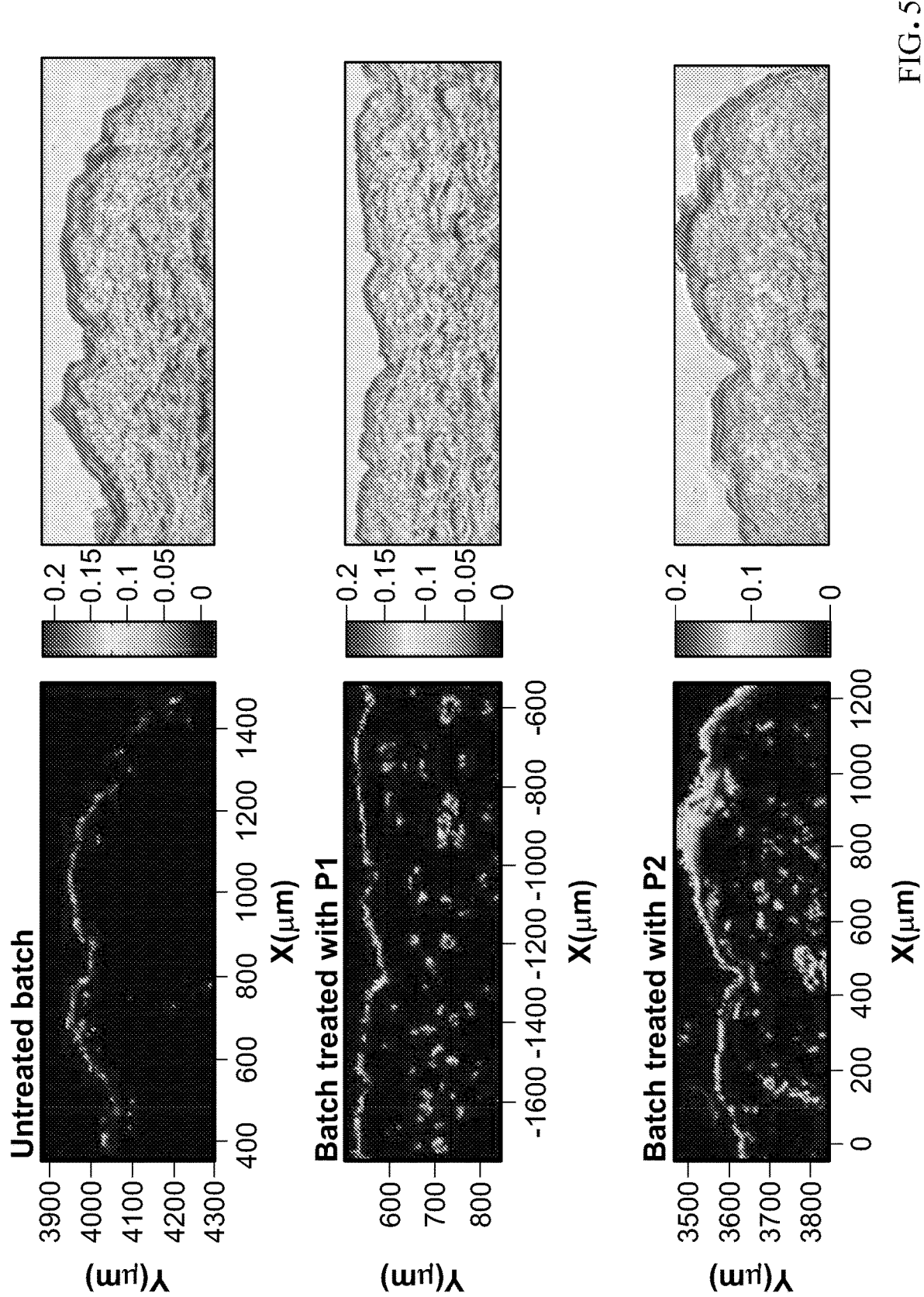
FIG. 5 illustrates the NCLS scores of the contributions of the active ingredient signature on each batch.

Classical least square (CLS) fitting with non-negativity constraints: For the spectral fitting at third analysis was realized: the Non-negativity Constrained Classical Least Squares (NCLS) analysis. It was a spectral unmixing method that aims to estimate the concentrations (or abundance fractions) of known spectral signatures in terms of measured linear mixings of these signatures. The originality of this method is that it adds to the classical least squares procedure a positivity constraint on concentrations. Computational details are reported in the literature (2009, Tfayli et al.). The NCLS fitting estimates a contribution percentages of reference spectra within each spectrum in the hyperspectral image. Given that some spectral features overlap between the skin and the principle active ingredient it is common to have some pixels with small percentage contribution in the control sample. For each pixel of the image, the positive abundance fractions of the reference spectra were estimated individually using the CLS algorithm. The scores of the contributions of the active ingredient signature on each batch are shown in FIG. 5.

On Day 1, on the blank batch TJ1, a very slight contribution of the active ingredient on the blank batch spectra was observed. On the batch P1J1, the NCLS score was moderate. On the batch P2J1, the NCLS score was fairly clear.

Analysis of NCLS scores: The analysis of the NCLS scores allows to semi-quantify the penetration of the active into the skin. It is possible then to determine a percentage of variation of active ingredient penetration between the batches P1 and P2.

The NCLS score of the different batches are shown here below:

|         | TJ1      | P1J1     | P2J1     |
|---------|----------|----------|----------|
| Average | 0.052683 | 0.117525 | 0.153203 |
| SEM     | 0.0062   | 0.004535 | 0.003135 |

Figure 6:
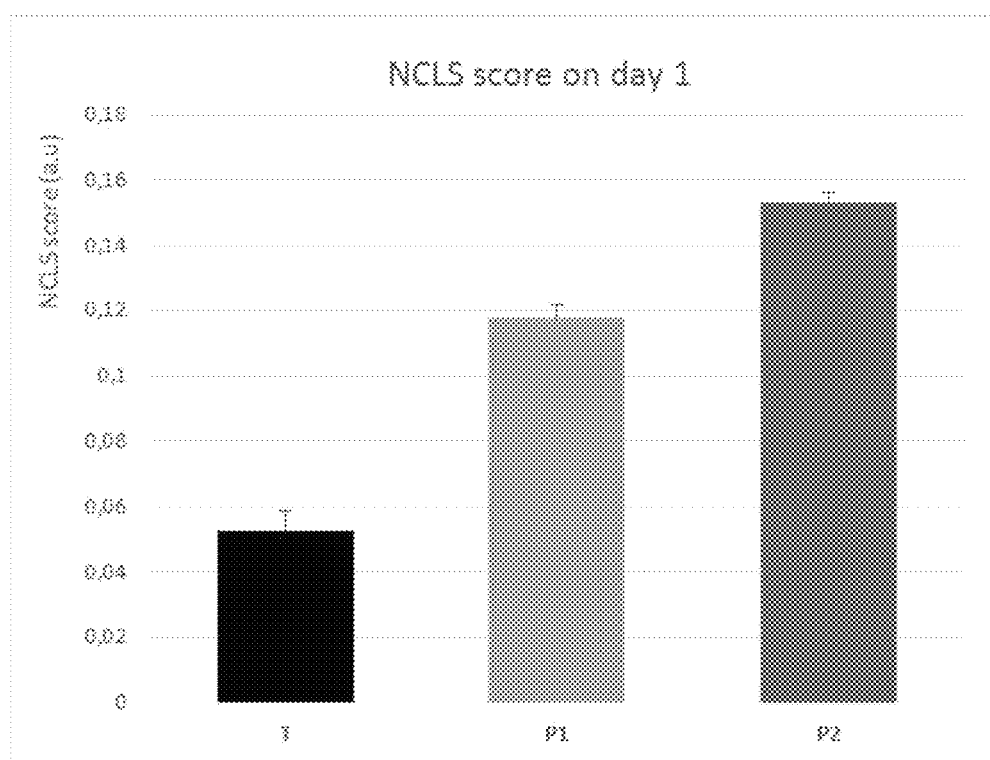
FIG. 6 also illustrates the NCLS score of the different batches.

The NCLS score of the different batches are also presented in FIG. 6. On the blank batch TJ1, the NCLS score was equal to 0.050607. The effect of product application on NCLS score was compared to the blank batch TJ1. The formulation P1 induced a significant increase of 123%. The formulation P2 induced a significant increase of 191%. When compared to the batch P1J1, the formulation P2 induced a significant increase of 30%. Thus, the formulation P2 induced a significant increase of the active ingredient penetration by 30% when compared to the formulation P1.

According to the experimental conditions described above: The penetration of the formulations A: NAD+, ref. 740103.00.0 at 5% in sterile distillate water (P1) and NAD+-Liposome Customized Development (P2) was assessed by following the band at ~1030 cm$^{-1}$, the band at 2930 cm$^{-1}$ and by analyzing the NCLS score, by infrared spectroscopy. Hyperspectral images enabled to detect the active ingredient thanks to the band at ~1030 cm$^{-1}$ under the skin surface. Its presence was more marked on skin sections treated with "P2" revealing a better penetration of the product NAD+–Liposome Customized Development (P2) compared to the formulation A: NAD+, ref. 740103.00.0 at 5% (P1). The analysis of NCLS score (contribution percentages of the active ingredient spectra within each spectrum in the hyperspectral images) determined that the product NAD+–Liposome Customized Development (P2) induced a significant increase by 30% of the active ingredient A: NAD+, ref. 740103.00. These results indicated that the liposomes present in the product P2 favor the penetration of NAD+ into the skin. It is noted that  is understood as p<0.01 (99%).

Cell Survival and Senescence Study

A study was performed to test the efficacy of a liposomal formulation of NAD+ on cell survival, NAD+ intracellular delivery and cellular senescence in primary human keratinocytes and endothelial cells.

Materials and Methods

Cell Cultures

Primary human aortic endothelial cells (HAECs) and human epidermal keratinocytes (HEKas) were purchased at Lonza, Basel, Switzerland. Adhering cells were grown to confluence in fibronectin-coated 75 cm$^2$ flasks in endothelial growth medium (EGM-2, Lonza) or dermal basal cell medium (DCBM, Lonza) for HAECs and HEKas, respectively. Media were supplemented with 10% fetal bovine serum (FBS).

Western Blot and Cell Survival Assay

Cells were detached by using Tripsin/EDTA and reseeded in 6-well plates (180,000/well). Cells were grown to 80% confluence and rendered quiescent for 24 h in medium containing 0.5% FBS. Next, cells were treated with NAD+ 200 µM or NAD+ in liposome matrix (LIPONAD) at different concentrations (1:1, 1:2 or 1:3) for 24 hours. Thereafter, supernatants were collected and cells were treated with lysis buffer containing Tris 50 mM, NaCl 150 mM, EDTA 1 mM, NaF 1 mM, DTT 1 mM, aprotinin 10 mg/mL, leupeptin 10 mg/mL, Na3VO4 0.1 mM, phenylmethylsulfonyl fluoride (PMSF) 1 mM, and NP-40 0.5%. Protein concentration was determined according to the manufacturer's recommendations (Bio-Rad Laboratories AG, Fribourg, Switzerland). About 20-30 µg of total protein lysates were separated on a 10% SDS-PAGE before being transferred to a polyvinylidene fluoride membrane using a wet transfer method (Bio-Rad). Membranes were incubated with primary antibodies against SIRT1 (1:1000, Abcam, Cambridge, UK) at 4° C. overnight on a shaker. The following incubation with secondary antibody (anti-mouse 1:2000, Southern Biotechnology, Birmingham, AL, USA) was done for 1 h at room temperature. Densitometric analyses were performed (Amersham Imager 600, GE Healthcare Europe GmbH, Glattbrugg, Switzerland), and protein expression was normalized to GAPDH. Lactic dehydrogenase (LDH) release was measured through colorimetric assay (Roce Diagnostics GmBH, Mannheim, Germany). Absorbance was measured using a 490 nm wavelength (reference >600 nm) in a microplate reader (Tecan, Männendorf, Switzerland). Absorbance values were normalized to a maximal release, obtained through a treatment with 1% TritonX-100. Cell survival was defined as (100-cell death %) and normalized to control.

Cell Senescence Assay

Cells were detached by using Tripsin/EDTA and reseeded in 2-well slides (100,000/well). Thereafter cells were treated with NAD+200 µM or NAD+200 µM+ LIPONAD 1:3 for 48 hours. Senescent cells were revealed through staining for senescence-associated β-galactosidase (SABG) (Merck KGaA, Darmstadt, Germany). The percentage of positively stained cells was counted in four visual fields for each slide using a microscope and normalized to control.

Statistical Analysis

Values are expressed as mean±SEM. A significance threshold for type I probability of error was set <0.05. Comparisons between two groups were performed using the unpaired t Test. Comparisons among multiple groups were performed using ANOVA test with Tukey post-hoc analysis.

Figure 7:
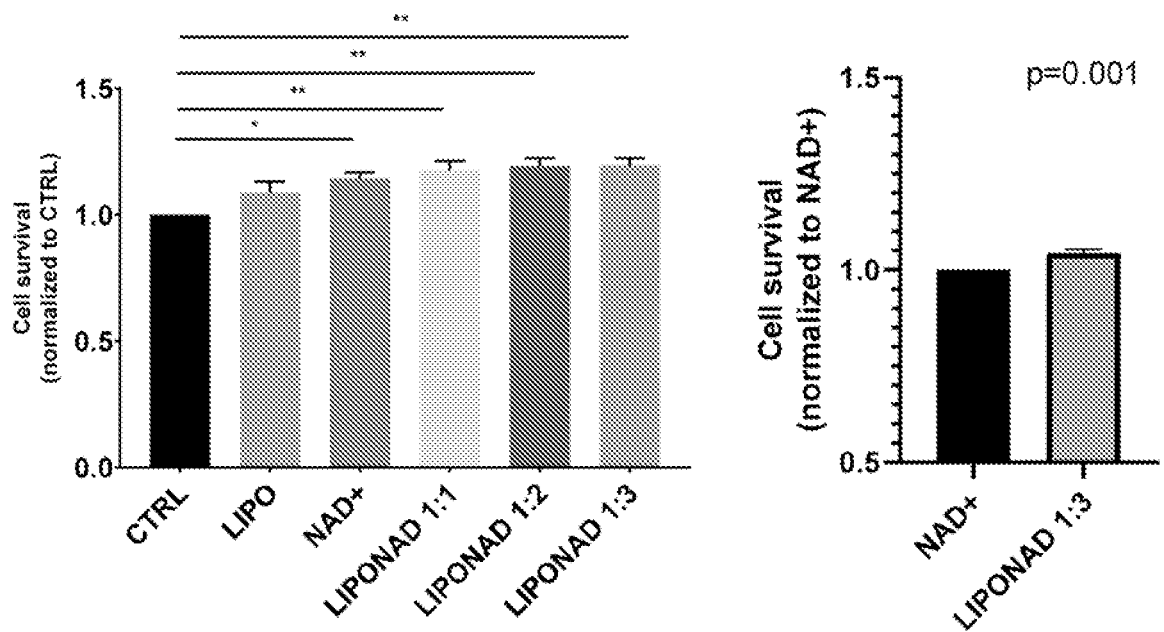
FIG. 7 is a graph representing the cell survival results in human aortic endothelial cells (HAECs).

Results: A significant increase of cell survival in HAECs treated with LIPONAD 1:3, compared to control (+19.5%; 95% C.I. 6.8-32.3%) and to NAD+ alone (+4.3%; 95% C.I. 1.2-7.4%) was seen. This is shown in FIG. 7. A non-significant increase was instead observed in HEKas.

NAD+ Intracellular Delivery

Intracellular delivery of NAD+ was measured through the induction of SIRT1 expression. No significant increase in SIRT1 expression was observed between treated and untreated cells, either in HAECs or in HEKAs. Additional tests are on the way whereby SIRT1 expression will me assayed by ELISA as opposed to western blotting.

Cellular Senescence

A significant reduction in the number of senescent cells was observed in both HAECs and in HEKas treated with LIPONAD 1:3. In particular, compared to control, the average reduction in the number of senescent cells was 51.3% (95% C.I. 3.9-63.9%) for HAECs and 36.6% (95% C.I. 1.6-66.3%) for HEKAs (FIGS. 2a and 3a). Compared to NAD+ alone, the average reduction was 28.7% (95% C.I. 9.4-33.9%) and 15.4% (95% C.I. 4.9-24.3%) for HAECs and HEKas, respectively. This can be seen in FIGS. 8 and 9.

These results show that the liposomal formulation of NAD+(LIPONAD) is superior to NAD+ alone in reducing cellular senescence of cultured human endothelial and epidermal cells. At the same time, it is superior to NAD+ alone in increasing cell survival of cultured human endothelial cells.

Based on the experimental results and from a translational perspective, it is believed that treatment with NAD+ LIPONAD is superior to NAD+ alone in slowing down skin aging. In particular, the results on endothelial cells suggest that NAD+ LIPONAD improves the function of the skin microcirculation, a crucial factor for skin tropism and tone.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A method of administration comprising topically administering to a subject in need thereof a composition comprising (i) a liposome comprising lecithin; (ii) a solvent comprising a combination of water, glycerin and pentylene glycol; (iii) tocopherol; (iv) a pH adjusting agent; and (v) an active agent encapsulated in the liposome, wherein the active agent comprises nicotinamide adenine dinucleotide (NAD+), wherein based on total weight of the composition:
    the NAD+ is in an amount from about 0.5 wt % to about 15 wt %,
    the lecithin is in an amount from about 0.5 wt % to about 15%,
    the water is in an amount from about 5% to about 40%,
    the glycerol is in an amount from about 30% to about 80%,
    the pentylene glycol is in an amount from about 0.5 wt % to about 15%,
    the tocopherol is in an amount up to about 0.5 wt %, and
    the pH adjuster is in an effective amount to adjust the pH of the composition to a range from about 4 to about 9.

2. The method of claim 1, wherein based on the total weight of the composition:
    the NAD+ is in an amount from about 1 wt % to about 10 wt %,
    the lecithin is in an amount from about 1 wt % to about 10%,
    the water is in an amount from about 10% to about 30%,
    the glycerol is in an amount from about 50% to about 70%,
    the pentylene glycol is in an amount from about 1 wt % to about 10%, and
    the tocopherol is in an amount up to about 0.3 wt %.

3. The method of claim 2, wherein the composition maintains more than about 90 wt %, more than about 92 wt %, more than about 94 wt %, more than about 96 wt %, more than about 98 wt %, more than about 99 wt %, or about 100 wt % of the active agent after storage at a temperature of about 2° C. to about 8° C. for a duration of about 1 month, about 3 months, about 6 months, or about 12 months, as compared to the weight of the active agent in the composition before storage (t=0).

4. The method of claim 2, wherein the composition maintains more than about 90 wt %, more than about 92 wt %, more than about 94 wt %, more than about 96 wt %, more than about 98 wt %, more than about 99 wt %, or about 100 wt % of the active agent after storage at a temperature of about 20° C. to about 30° C. for a duration of about 1 month, about 3 months, about 6 months, or about 12 months, as compared to the weight of the active agent in the composition before storage (t=0).

5. The method of claim 2, wherein the composition maintains more than about 90 wt %, more than about 92 wt %, more than about 94 wt %, more than about 96 wt %, more than about 98 wt %, more than about 99 wt %, or about 100 wt % of the active agent after storage at a temperature of about 35° C. to about 45° C. for a duration of about 1 month, about 3 months, about 6 months, or about 12 months, as compared to the weight of the active agent in the composition before storage (t=0).

* * * * *